(12) United States Patent
Chaudry

(10) Patent No.: US 8,309,061 B2
(45) Date of Patent: *Nov. 13, 2012

(54) FORMULATIONS AND METHODS FOR TREATING RHINOSINUSITIS

(75) Inventor: Imtiaz Chaudry, American Canyon, CA (US)

(73) Assignee: Dey Pharma, L.P., Basking Ridge, NJ (US)

( * ) Notice: Subject to any disclaimer, the term of this patent is extended or adjusted under 35 U.S.C. 154(b) by 946 days.

This patent is subject to a terminal disclaimer.

(21) Appl. No.: 11/078,263

(22) Filed: Mar. 12, 2005

(65) Prior Publication Data

US 2005/0180925 A1 Aug. 18, 2005

Related U.S. Application Data

(63) Continuation-in-part of application No. 10/657,550, filed on Sep. 4, 2003, which is a continuation-in-part of application No. 10/414,682, filed on Apr. 16, 2003, which is a continuation-in-part of application No. 10/414,756, filed on Apr. 16, 2003, now Pat. No. 7,811,606.

(51) Int. Cl.
*A61K 9/14* (2006.01)
*A61K 31/56* (2006.01)
(52) U.S. Cl. .......................... 424/46; 424/489; 514/177
(58) Field of Classification Search .................. None
See application file for complete search history.

(56) References Cited

U.S. PATENT DOCUMENTS

| | | | |
|---|---|---|---|
| 3,091,569 A | 5/1963 | Sheffner |
| 5,174,475 A | 12/1992 | Day et al. |
| 5,593,688 A | 1/1997 | Baldeschwieler |
| 5,858,330 A | 1/1999 | Boltri et al. |
| 5,958,378 A | 9/1999 | Waldrep et al. |
| 5,976,573 A | 11/1999 | Kim |
| 5,993,781 A | 11/1999 | Snell et al. |
| 6,113,894 A | 9/2000 | Smith |
| 6,207,703 B1 | 3/2001 | Ponikau |
| 6,241,969 B1 | 6/2001 | Saidi et al. |
| 6,291,500 B2 | 9/2001 | Ponikau |
| 6,368,616 B1 | 4/2002 | Doi |
| 6,410,062 B1 | 6/2002 | Callaghan et al. |
| 6,464,958 B1 | 10/2002 | Bernini et al. |
| 6,465,709 B1 | 10/2002 | Sun et al. |
| 6,509,028 B2 | 1/2003 | Williams et al. |
| 6,555,566 B2 | 4/2003 | Ponikau |
| 6,608,054 B2 | 8/2003 | Meade et al. |
| 7,811,606 B2 | 10/2010 | Chaudry |
| 2001/0002404 A1 | 5/2001 | Webb et al. |
| 2001/0008632 A1 | 7/2001 | Freund et al. |
| 2002/0006944 A1 | 1/2002 | Ohkawa et al. |
| 2002/0010208 A1 | 1/2002 | Shashoua et al. |
| 2002/0013331 A1 | 1/2002 | Williams et al. |
| 2002/0052390 A1 | 5/2002 | Ponikau |
| 2002/0061281 A1 | 5/2002 | Osbakken et al. |
| 2002/0071874 A1 | 6/2002 | Olejnik et al. |
| 2002/0124820 A1 | 9/2002 | Kreuter |
| 2002/0136918 A1 | 9/2002 | Akutsu et al. |
| 2002/0177609 A1 | 11/2002 | Swindell et al. |
| 2002/0192288 A1 | 12/2002 | Williams et al. |
| 2002/0198209 A1 | 12/2002 | Woodward et al. |
| 2003/0017199 A1 | 1/2003 | Woodward et al. |
| 2003/0065023 A1 | 4/2003 | Swindell et al. |
| 2003/0222364 A1 | 12/2003 | Jackson et al. |
| 2004/0045805 A1 | 3/2004 | Lancaster et al. |
| 2004/0081626 A1 | 4/2004 | Watanabe et al. |
| 2004/0136918 A1 | 7/2004 | Garrett et al. |
| 2004/0141925 A1 | 7/2004 | Bosch et al. |
| 2007/0140980 A1 | 6/2007 | Capocchi et al. |
| 2008/0050442 A1 | 2/2008 | Chaudry |

FOREIGN PATENT DOCUMENTS

| | | |
|---|---|---|
| CA | 2 522 292 A1 | 10/2004 |
| CN | 1282251 A | 1/2001 |
| CN | 1335766 A | 2/2002 |
| CN | 1409627 A | 4/2003 |
| EP | 0 343 268 | 11/1989 |
| EP | 0 385 445 A2 | 9/1990 |
| JP | 1-100120 A | 4/1989 |
| JP | 03-165833 | 7/1991 |
| JP | 5-506642 | 9/1993 |
| JP | 07-053358 | 2/1995 |
| JP | 10-500420 | 1/1998 |
| JP | 11-130659 A | 5/1999 |
| JP | 11-514979 A | 12/1999 |
| JP | 2000-508675 A | 7/2000 |
| JP | 2001-002589 | 1/2001 |
| JP | 2001-520188 A | 10/2001 |
| JP | 2001-523638 | 11/2001 |
| JP | 2002-539154 | 11/2002 |

(Continued)

OTHER PUBLICATIONS

Bernstein, Is the use of benzalkonium chloride as a preservative . . . (J. Allergy. Clin. Immunol., 105(1), 39-44, 2000).*
Family Practice Notebook.com—Systematic Corticosteroid—http://www.fpnotebook.com/END118.htm.
Family Practice Notebook.com—Allergic Fungal Sinusitis—http://www.fpnotebook.com/ENT151.htm.
Family Practice Notebook.com—Inhaled Corticosteroid—http://www.fpnotebook.com/LUN112.htm.
Americas Family Physician—Jan. 1, 2001—Adult Rhinosinusitis: Diagnosis and Management—J. David Osguthorpe, M.D., Medical University of South Carolina, Charleston, South Carolina—http://www.aafp.org/afp/20010101/69.html.
The Diagnosis and Incidence of Allergic Fungal Sinusitis—Jens U. Ponikau, MD; David A. Sherris, MD; Eugene B. Kern, MD; Henry A. Homburger, MD; Evangelos Frigas, MD; Thomas A. Gaffey, MD; and Glenn D. Robers, PhD—1999 Mayo Foundation for Medical Education and Research—May Clin. Proc, Sep. 1999, vol. 74.

(Continued)

*Primary Examiner* — David J Blanchard
*Assistant Examiner* — Tigabu Kassa
(74) *Attorney, Agent, or Firm* — Alston & Bird LLP

(57) ABSTRACT

The invention involves methods and formulations for treating or preventing rhinosinusitis, including but not limited to, bacterial-induced, viral-induced and/or fungus-induced rhinosinusitis in mammals, and/or rhinosinusitis not induced by an infective agent, such as bacteria, fungus or virus. In one embodiment, the formulation of the present invention comprises an anti-inflammatory agent (e.g. fluticasone propionate) having a specific particle size distribution profile. The formulation may also comprise an antifungal agent, antibiotic or antiviral agent.

16 Claims, No Drawings

FOREIGN PATENT DOCUMENTS

| | | |
|---|---|---|
| JP | 2003-506396 | 2/2003 |
| JP | 2005-503378 | 2/2005 |
| JP | 2005-506369 | 3/2005 |
| WO | WO 86/03750 | 7/1986 |
| WO | WO 92/04365 | 8/1992 |
| WO | WO 92/17183 | 10/1992 |
| WO | WO 95/31964 A1 | 11/1995 |
| WO | WO 97/08950 A1 | 3/1997 |
| WO | WO 99/18971 * | 4/1999 |
| WO | WO 99/20261 A2 | 4/1999 |
| WO | WO 00/12063 A1 | 3/2000 |
| WO | WO 00/25746 | 5/2000 |
| WO | WO 00/27363 | 5/2000 |
| WO | WO 01/10409 A1 | 2/2001 |
| WO | WO 01/13885 A1 | 3/2001 |
| WO | WO 01/32125 | 5/2001 |
| WO | WO 01/49263 | 7/2001 |
| WO | WO 01/78743 A1 | 10/2001 |
| WO | WO 02/00199 | 1/2002 |
| WO | WO 02/055136 A2 | 7/2002 |
| WO | WO 02/072066 A1 | 9/2002 |
| WO | WO 03/013434 A2 | 2/2003 |
| WO | WO 03/020219 A2 | 3/2003 |
| WO | WO 03/035062 A1 | 5/2003 |

OTHER PUBLICATIONS

UTMB—The University of Texas Medical Branch—Rhinosinusitis: Current Concepts; Frederick S. Rosen, MD, Mathew Ryan MD.

Allergic Diseases Resource Center: Rhinosinusitis—Rhinosinusitis: Synopsis http://www.worldallergy.org/professional/allergic_diseases_center/rhinosinusitis/sinusitiss . . . .

Mayo Clinic, Rochester, Minnesota—Mayo Clinic Receives Patent for New Treatment of Chronic Sinus Infection Apr. 30, 2003—http://www.mayclinic.org/news2003-rst/1772.html.

NCBI—PubMed—Improved method for estimation of azole antifungal inhibitory concentrations against *Candida* Species, based on azole/antibiotic interactions; Odds FC, Abbot AB, Pye G., Troke PF.; Mar. 17, 2003.

NCBI—PubMed—Chronic invasive fungal rhinosinusitis—Stringer SP, Ryan MW; http://www.ncbi.nlm.nih.gov/entrez/query.fcgi?cmd_Retrieve&db=PubMed&List_uids-10 . . . .

NCBI—PubMed—Acute invasive fungal rhinosinusitis—case report; Jedrusik A, Galewicz A, Krzeski A, Dwilewicz-Trojaczek J. Deptala A, Michalik J; http://www.ncbi.nlm.nih.gov/entrez/query.fcgi?cmd_Retrieve&db=PubMed&List_uids-12.

NCBI—PubMed—Intransal antifungal treatment in 51 patients with chronic rhinosinusitis; Ponikau JU, Sherris DA, Kita H, Kern EB; http://www.ncbi.nlm.nih.gov/entrez/query.fcgi?cmd_Retrieve&db=PubMed&List_uids-12.

NCBI—PubMed—Energing and less common fungal pathogens; Fleming RV, Walsh TJ, Anaissie EJ; http://www.ncbi.nlm.nih.gov/entrez/query.fcgi?cmd_Retrieve&db=PubMed&List_uids-12.

NCBI—PubMed—Topical antibiotic antifungal, and antiseptic solutions decrease ciliary activity in nasal respiratory cells; Gosepath J, Grebneva N, Mossikhin S, Mann WJI; http://www.ncbi.nlm.nih.gov/entrez/query.fcgi?cmd_Retrieve&db=PubMed&List_uids-11.

NCBI—PubMed—Chronic invasive fungal sinusitis: a report of two atypical cases; Busaba NY, Colden DG, Faquin WC, Salman SD; http://www.ncbi.nlm.nih.gov/entrez/query.fcgi?cmd_Retrieve&db=PubMed&List_uids-12.

NCBI—PubMed—Rhinocerebral mucormycosis in the era of lipid-based amphotericin B: case report and literature review; Mondy KE, Haughey B, Custer PL, Wippold FJ 2nd, Ritchie DJ, Mundy LM; http://www.ncbi.nlm.nih.gov/entrez/query.fcgi?cmd_Retrieve&db=PubMed&List_uids-11.

NCBI—PubMed—Effect of anti-fungal nasal lavage with amphotericin B on nasal polyposis; Ricchetti A, Landis BN, Maffioli A, Giger R, Zeng C, Lacroix JS; http://www.ncbi.nlm.nih.gov/entrez/query.fcgi?cmd_Retrieve&db=PubMed&List_uids-11.

NCBI—PubMed—Paranasal sinus mucormycosis: a report of two cases; Ruoppi P, Dietz A, Nikanne E, Seppa J, Markkanen H, Nuutinen J; http://www.ncbi.nlm.nih.gov/entrez/query.fcgi?cmd_Retrieve&db=PubMed&List_uids-11.

NCBI—PubMed—A case report of allergic fungal sinusitis caused by *Penicillium* sp. and *Cladosporium* sp; Matsuwaki Y, Nakajima T, Lida M, Nohara O, Haruna S, Moriyama H http://www.ncbi.nlm.nih.gov/entrez/query.fcgi?cmd_Retrieve&db=PubMed&List_uids-11.

NCBI—PubMed—Acute fulminant fungal sinusitis: clinical presentation, radiological findings and treatment; Sohail MA, Al Khabori M, Hyder J, Verma A; http://www.ncbi.nlm.nih.gov/entrez/query.fcgi?cmd_Retrieve&db=PubMed&List_uids-11.

NCBI—PubMed—Treatment of invasive fungal sinusitis with liposomal amphotericin B: a report of four cases; Sungkanuparph S, Sathpatayavongs B, Kunachak S, Luxameechanporn T, Cheewaruangroj W; http://www.ncbi.nlm.nih.gov/entrez/query.fcgi?cmd_Retrieve&db=PubMed&List_uids-11.

NCBI—PubMed—Fungal infections of the paranasal sinuses; Karci B, Burhanoglu D, Erdem T, Hilmioglu S, Inci R, Veral A; http://www.ncbi.nlm.nih.gov/entrez/query.fcgi?cmd_Retrieve&db=PubMed&List_uids-11.

NCBI—PubMed—Case report. Successful outcome of invasive nasal sinus zygomycosis in a child with relapsed acute lymphoblastic leukaemia due to liposomal ampohtericin B; Wali YA, al LamkiZ, al Kindi H, Taqi AM, Shah W, Soliman H, Zacharia M, al Okbi H; http://www.ncbi.nlm.nih.gov/entrez/query.fcgi?cmd_Retrieve&db=PubMed&List_uids-11.

NCBI—PubMed—Aggressive combination treatment for invasive fungal sinusitis in immunocompromised patients; Rizk SS, Krasu DH, gerresheim G, Mudan S; http://www.ncbi.nlm.nih.gov/entrez/query.fcgi?cmd_Retrieve&db=PubMed&List_uids-10.

NCBI—PubMed—Efficacy of FK463, a new lipopeptide antifungal agnet, in mouse models of pulmonary aspergillosis; Matsumoto S, Wakai Y, Nakai T, Hatano K, Ushitani T, Ikeda F, Tawara S, Goto T, Matsumoto F, Kuwahara S; http://www.ncbi.nlm.nih.gov/entrez/query.fcgi?cmd_Retrieve&db=PubMed&List_uids-10.

NCBI—PubMed—Report of two rare cases of fungal sinusitis; Moriyama, Watanabe T, Kodama S, Suzuki M, Mogi G; http://www.ncbi.nlm.nih.gov/entrez/query.fcgi?cmd_Retrieve&db=PubMed&List_uids-10.

NCBI—PubMed—Successful treatment of a invasive aspergillosis of the skull base and paranasal sinuses with liposomal amphotericin B and itraconazole; Streppel M, Bachmann G, Arnold G, Damm M, Stennert E; http://www.ncbi.nlm.nih.gov/entrez/query.fcgi?cmd_Retrieve&db=PubMed&List_uids-10.

NCBI—PubMed—Successful Treatment of *Mucormycosis* and *Aspergillus* sp. Rhinosinusitis in an Immunocompromised Patient; Borges V Neto, Medeiros S. Ziomkowki S, Machado A; http://www.ncbi.nlm.nih.gov/entrez/query.fcgi?cmd_Retrieve&db=PubMed&List_uids-11.

NCBI—PubMed—Report of the first case of invasive fungal sinusitis caused by *Scopulariopsis acremonium*; review of *scopulariopsis* infections; Ellison MD, Hung RT, Harris K, Campbell BH; http://www.ncbi.nlm.nih.gov/entrez/query.fcgi?cmd_Retrieve&db=PubMed&List_uids-97.

NCBI—PubMed—Successful program to prevent *aspergillus* infections in children undergoing marrow transplantation: use of nasal amphotericin; Trigg ME, Morgan D, Burns TL, Kook H, Rumelhart SL, Holida MD, Giller RH; http://www.ncbi.nlm.nih.gov/entrez/query.fcgi?cmd_Retrieve&db=PubMed&List_uids-90.

NCBI—PubMed—*Aspergillus* sinusitis: clinical aspects and treatment outcomes; Min YG, HKim HS, Lee KS, Kang MK, Han MH; http://www.ncbi.nlm.nih.gov/entrez/query.fcgi?cmd_Retrieve&db=PubMed&List_uids-87.

NCBI—PubMed—Antifungal activity against allergic fungal sinusitis organisms; Bent JP 3rd, Kuhn FA; http://www.ncbi.nlm.nih.gov/entrez/query.fcgi?cmd_Retrieve&db=PubMed&List_uids-89.

NCBI—PubMed—Liposomal amphotericin B (AmBisome) in the treatment of complicated kala-azar under filed conditions; Seamans J, Boer C, Wilkinson R, de Jong J, de Wilde E, Sondorp E, Davidson R.

NCBI—Successful treatment of sinusitis caused by *Cunninghamella bertholletiae*; Ng TT, Campbell CK, Rothera M, Houghton JB, Hughes D, Denning DW; http://www.ncbi.nlm.nih.gov/entrez/query.fcgi?cmd_Retrieve&db=PubMed&List_uids-79.

NCBI—Invasive ottits externa due to *Aspergillus* species: case report and review; Godon G, Gidding NA.

NCBI—PubMed—Invasive fungal sinusitis in patients undergoing bone marrow transplantation; Drakos PE, Nagler A, On R, Naparstek E, Kapelushnik J, Engelhard D, Rahv G, Ne'emean D, Slavin S; http://www.ncbi.nlm.nih.gov/entrez/query.fcgi?cmd_Retrieve&db=PubMed&List_uids-82.

NCBI—PubMed—New methods of delivery of amphotericin B; Schmitt HJ; http://www.ncbi.nlm.nih.gov/entrez/query.fcgi?cmd_Retrieve&db=PubMed&List_uids-82.

NCBI—PubMed—Oral itraconazole plus nasal ampohtericin B for prophylaxis of invasive aspergillosis in patients with hematological malignancies; Todeschini G, Murari C, Boneis R, Pizzolo G, Amaddi G, Ambrosetti A, Ceru S, Piacentini I, Martini N, Montresor P, et al.

NCBI—PubMed—Infection due to the fungus *Acremonium* (*cephalosporium*) Fincher RM, Fisher JF, Lovel RD, Newman CL, Espinel-Ingroff A, Shadomy HJ http://www.ncbi.nlm.nih.gov/entrez/query.fcgi?cmd_Retrieve&db=PubMed&List_uids-19.

NCBI—PubMed—Intranasal amphotericin B reduces the frequency of invasive aspergillosis in neutropenic patients; Jeffery GM, Beard ME, Ikram RB, Chua J, Allen JB, Heaton DC, Hart DN, Schousboe MI; http://www.ncbi.nlm.nih.gov/entrez/query.fcgi?cmd_Retrieve&db=PubMed&List_uids-20.

NCBI—PubMed—Antifungal and surgical treatment of invasive aspergillosis; review of 2,121 published cases; Denning DW, Stevens DA; http://www.ncbi.nlm.nih.gov/entrez/query.fcgi?cmd_Retrieve&db=PubMed&List_uids-22.

NCBI—PubMed—Intraconazole therapy in aspergillosis: study in 49 patients; Dupont B; http://www.ncbi.nlm.nih.gov/entrez/query.fcgi?cmd_Retrieve&db=PubMed&List_uids-21.

NCBI—PubMed—Comparison of oral fluconazole and amphotericin B prophylaxis against fungal infections in the neutropenic phase of patients treated with antileukemic agents; Finke R; http://www.ncbi.nlm.nih.gov/entrez/query.fcgi?cmd_Retrieve&db=PubMed&List_uids-21.

NCBI—PubMed—Fungal diseases of the sinuses; Corey JP, Romberger CF, Shaw GY; http://www.ncbi.nlm.nih.gov/entrez/query.fcgi?cmd_Retrieve&db=PubMed&List_uids-21.

NCBI—PubMed—Decrease in systematic fungal infections in hematogical neoplasms with empirical use of amphotericin B therapy; Zimmermann-Holsi MB, Stahel RA, Vogt P, Oelz O; http://www.ncbi.nlm.nih.gov/entrez/query.fcgi?cmd_Retrieve&db=PubMed&List_uids-29.

NCBI—PubMed—Allergic fungal sinusitis; Philip G, Keen CE; http://www.ncbi.nlm.nih.gov/entrez/query.fcgi?cmd_Retrieve&db=PubMed&List_uids-27.

NCBI—PubMed—Nonsurgical treatment of sinusitis; Malow JB, Creticos CM; http://www.ncbi.nlm.nih.gov/entrez/query.fcgi?cmd_Retrieve&db=PubMed&List_uids-27.

NCBI—PubMed—New methods for delivery of antifungal agents; Meunier F; http://www.ncbi.nlm.nih.gov/entrez/query.fcgi?cmd_Retrieve&db=PubMed&List_uids-26.

NCBI—PubMed—Improved diagnosis and prognosis of mucormycosis. A clinicopathologic study of 33 cases; Parfrey NA; http://www.ncbi.nlm.nih.gov/entrez/query.fcgi?cmd_Retrieve&db=PubMed&List_uids-39.

NCBI—PubMed—Aspergillosis of themaxillary sinuses in otherwise healthy patients; Meikle D, Yarington CT Hr, Winterbauer RH; http://www.ncbi.nlm.nih.gov/entrez/query.fcgi?cmd_Retrieve&db=PubMed&List_uids-40.

NCBI—PubMed—Primary pituitary aspergillosis responding to transsphenoidal surgery and combined therapy with amphotericin-B and 5-fluorcytosine: case report.

NCBI—PubMed—Patient survival factors in paranasal sinus mucormycosis; Bletzer A, Lawson W, Meyers BR, Biller HF; http://www.ncbi.nlm.nih.gov/entrez/query.fcgi?cmd_Retrieve&db=PubMed&List_uids-73.

Invasive *aspergillus* rhinosinusitis in patients with acute leukemia (Mar.-Apr. 13, 1991) http://www.ncbi.nlm.nih.gov/entrez/query.fcgi?cmd_Retrieve&db=PubMed&List_uids-19.

Efficacy of Sch39304 in murine cyptococcosis (Aug. 1989) http://www.ncbi.nlm.nih.gov/entrez/query.fcgi?cmd_Retrieve&db=PubMed&List_uids-25.

"BECONASE AQ®" from the online Physician's Desk Reference (PDR®)—accessed Nov. 19, 2007.

Chervinsky, P., "Clinical Review of Once-Daily Beclomethasone Dipropionate for Seasonal Allergic Rhinitis", Clinical Therapeutics, 1996, 18(5), pp. 790-796.

FLONASE® from the online Physician's Desk Reference (PDR®)—accessed Dec. 1, 2007.

Lacy, C. et al., 1999-2000 Drug Information Handbook, Lexi-Comp, Inc., Cleveland, 1999, pp. 112-114.

Lacy, C. et al., Drug Information Handbook, Lexi-Comp, Inc., Cleveland, 1999, pp. 445-446.

Merriam-Webster's Collegiate Dictionary, $10^{th}$ edition, Merriam-Webster Incorporated: Springfield, Massachusetts, 1993, p. 311.

Lacy et al., 1999-2000 Drug Information Handbook, Lexi-Comp, Inc., Aug. 21, 1999, pp. 26-28, 2225-2226, 453-456, 463-464 and 721-722.

Walker, Management of Allergic Rhinitis, Nursing Times, Aug. 21, 2003, 99(23).

Humuy et al., Topical Antiviral Agents for Herpes Simplex Virus Infections, Drugs Today, Aug. 21, 1998, 34(12).

Vippagunta et al., Crystalline Solids, Advanced Drug Delivery Reviews, Aug. 21, 2001, 48, pp. 3-26.

Office Action dated Jul. 12, 2010, and issued in connection with corresponding Canadian Application No. 2,522,294.

Office Action mailed Aug. 6, 2010, and issued in connection with corresponding U.S. Appl. No. 10/657,550.

Parikh, A., et al.; Topical corticosteroids in chronic rhinosinusitis: a randomized, double-blind, placebo-controlled trial using fluticasone propionate aqueous nasal spray; Rhinology, 39; 2001; pp. 75-79.

Office Action for Japanese Application No. 2006-504903 dated Aug. 4, 2010.

Office Action for Japanese Application No. 2006-504901 dated Aug. 4, 2010.

Office Action for Japanese Application No. 2006-504902 dated Aug. 4, 2010.

Office Action for Japanese Application No. 2006-516000 dated Sep. 8, 2010.

Dyson, G. et al., *Chemistry of Synthetic Drugs*, "Mir", 1964, pp. 12-16.

Drug Information Handbook, Lacy, C. et al., Lexi-Comp, Inc., Cleveland, 1993, pp. 397.

Vervloet et al., "Intranasal Fluticasone Once Daily Compared with Once-daily Cetirizine in the Treatment of Seasonal Allergic Rhinitis: Results of a Multicentre, Double-Blind Study," Clinical Drug Investigation, 1997, 13(6), pp. 291-298.

Waligorski et al., Raman Chemical Imaging of Complex Pharmaceutical Products. [online], [retrieved on Jan. 4, 2010]. Retrieved from the internet <http://www.chemimage.com/docs/posters/Pharmaceutical/RCI_of_Complex_Pharmaceutical_Products.pdf>.

Comparison of Drug Particle Sizing of Innovator and Generic Nasal Spray Formulations Based on Raman Chemical Imaging. [online], [retrieved on Jan. 4, 2010]. Retrieved from the Internet <http://www.chemimage.com/docs/white-papers/CI_Inhalation_ISPS_White_Paper.pdf>.

Office Action for Russian Application No. 2005 135 333 dated Dec. 17, 2008.

Office Action for Russian Application No. 2005 135 332 dated Sep. 29, 2008.

Office Action for Russian Application No. 2005 135 332 dated Dec. 21, 2007.

Encyclopaedia of Medical Terms, edited by the member of the Russian Academy of Medical Sciences V.A. Pokrovsky, second edition, M., "Medicina", 2001, pp. 697-698.

Russian Office Action for Russian Application No. 2005 135 333.

* cited by examiner

FORMULATIONS AND METHODS FOR TREATING RHINOSINUSITIS

RELATED APPLICATIONS

The present application is a continuation-in-part of application Ser. No. 10/657,550 filed Sep. 4, 2003, which is a continuation-in-part of application Ser. No. 10/414,682 and application Ser. No. 10/414,756 now U.S. Pat. No. 7,811,606, both filed Apr. 16, 2003. Each above-cited application is incorporated herein by reference in its entirety.

FIELD OF THE INVENTION

The present invention relates to formulations and methods for treating rhinosinusitis in mammals (e.g., humans), including but not limited to, bacterial, viral and/or fungus-induced rhinosinusitis, and/or non-bacterial, non-viral or non-fungus induced rhinosinusitis. The formulations of the present invention comprise a steroidal agent, including but not limited to, fluticasone beclomethasone, or mometasone. The steroidal agent may have a specific particle size distribution profile. The formulations may also comprise an antibiotic, antifungal agent or an antiviral agent, or any combination thereof. In one alternative embodiment of the present invention, the present formulations may take any form, preferably they are provided as a sterile, aqueous suspension or solution that can be administered intranasally via spray pump, nebulizer or any other suitable delivery device. In addition, the steroidal agent may be administered alone or in conjunction with an antifungal, antibiotic or antiviral agent.

BACKGROUND OF THE INVENTION

Rhinosinusitis is generally described as a group of disorders characterized by inflammation of the nasal mucosa and/or the paranasal sinuses. Chronic rhinosinusitis (CRS), for example, is diagnosed when signs or symptoms of inflammation persist for 8-12 weeks or longer. It is estimated that one out of every seven Americans suffers from chronic rhinosinusitis (CRS). Symptoms of CRS include nasal obstruction, loss of sense of smell, nasal or postnasal discharge, nasal congestion, and facial pain/pressure (typically over the affected sinus area).

CRS impairs normal physical and social functioning, and patients with CRS typically suffer from an overall poor quality of life. Moreover, CRS is often associated with other co-morbid conditions such as asthma, eczema and other media. Asthma is found in 20-35% of patients with CRS, and CRS is found in up to 75% of moderate-to severe asthmatics.

In some instances, it is now known that rhinosinusitis may be caused by fungi found in mucus. One type of fungus-induced rhinosinusitis is allergic fungus rhinosinusitis (AFS). AFS is generally diagnosed by: (1) the presence of nasal polyps; (2) allergic mucin; (3) CRS evidenced by CT scan; (4) positive fungal culture or histology; and/or (5) allergy to fungi by history, skin prick test or serology. AFS often leads to or is associated with CRS.

Current treatments for fungus-induced rhinosinusitis include antifungal medications to remove the antigenic burden. A topical or systemic corticosteroid may also be prescribed to control inflammation of the mucosal tissue associated with CRS. This inflammation is thought to contribute to tissue and bone destruction associated with CRS. Steroidal anti-inflammatories, including but not limited to fluticasone propionate and beclomethasone dipropionate having a particular particle size distribution profile may provide increased bioavailability, increased efficacy and/or prolonged therapeutic effect when administered intranasally.

CRS may also be characterized by or associated with a chronic bacterial infection of the sinuses (nasal-paranasal region) which is often superimposed upon a self-perpetuating, eosinophil-rich inflammatory process in the sinuses. Currently, antibiotic therapy is indicated for up to six weeks or more for the treatment and elimination of the bacterial infection associated with CRS.

SUMMARY OF INVENTION

The present invention relates generally to formulations and methods for treating rhinosinusitis in mammals (e.g., humans), including, but not limited to, bacterial-induced, viral-induced or fungus-induced rhinosinusitis and/or non-bacterial or non-fungus induced rhinosinusitis. In one embodiment, the formulations of the present invention comprise an anti-inflammatory agent, alone or in combination with an antifungal agent, antibiotic and/or antiviral agent. Ine one embodiment, it is believed that treating the patient with an antifungal agent will sufficiently reduce the level of fungal organisms in the patient's mucus such that the one ore more of the symptoms of rhinosinusitis are prevented from developing, or are lessened, or are prevented from worsening.

It is also believed that treating the patient with an anti-inflammatory agent (alone) will sufficiently reduce the one or more symptoms of non-fungal, non-bacterial or non-viral induced rhinosinusitis, including but not limited to, inflammation, discomfort, headache, or pain, for example. Here, the symptoms may be prevented from developing, or are lessened, or are prevented from worsening.

In an embodiment, the present formulations comprise about 4 mg to about 30 mg of the anti-fungal agent amphotericin $\beta$. In an alternative embodiment, the formulation of the present invention comprises about 10 to about 70 mg of the anti-fungal agent fluconazole or itraconazole.

The present invention is also based on the realization that a patient or individual may have already developed one or more symptoms of rhinosinusitis, possibly non-fungal or non-bacterial induced rhinosinusitis, when he or she first seeks the help of a physician or by the time, that treatment is started. Thus, it would also be beneficial to provide an anti-inflammatory steroid to the patient to treat inflammation of the mucosal tissue associated with rhinosinusitis, since such inflammation might lead to or contribute to tissue and bone destruction in the nasal-paranasal region, as well as discomfort, pain or headache.

Certain anti-inflammatories having a specific particle size distribution profile may provide increased bioavailability, increased efficacy or prolonged therapeutic effect when administered intranasally. In one embodiment, the formulation of the present invention comprises about 10 mcg to about 2000 mcg of an anti-inflammatory agent, including but not limited to, fluticasone, or a pharmaceutically acceptable derivative thereof, having the following particle size distribution profile: preferably about 10% of the drug substance particles have a particle size of about 0.40 microns; about 25% of the drug substance particles have a particle size of less than 1.4 microns; about 50% of the drug substance particles have a particle size of less than 2.5 microns; about 75% of the drug substance particles have a particle size of less than 4.0 microns; about 90% of the drug substance particles have a particle size of less than 6.0 microns.

In an alternative embodiment, the formulation of the present invention comprises about 0.2 mcg to about 3 mcg of the steroidal anti-inflammatory beclomethasone, or a pharmaceutically acceptable derivative thereof, having the following particle size distribution profile: about 10% of the drug substance particles have a particle size of about 0.4 microns; about than 25% of the drug substance particles have a particle size of less than 1.4 microns; about 50% of the drug substance particles have a particle size of less than 2.5 microns; about 75% of the drug substance particles have a particle size of less than 4.0 microns; about 90% of the drug substance particles have a particle size of less than 6.0 microns; and, greater than 90% or about 100% of the drug substance particles have a particle size of less than 10 microns.

In many instances, the fungus-induced rhinosinusitis may be accompanied by, or associated with, a bacterial infection of the nasal-paranasal mucosa. In one embodiment, the formulations of the present invention comprise an antibiotic. In an alternative embodiment, the present formulations may comprise about 1 to about 800 mg of the antibiotic neomycin sulfate.

In one embodiment, the formulations of the present invention may be provided in any form, which directly or indirectly contacts the formulation with the nasal mucosa and/or paranasal sinuses. In one embodiment, the present formulation is provided as a sterile aqueous solution or suspension. In an alternative embodiment, the formulation is in a metered dose spray pump, or through a device used for nebulization, for example.

The present invention also generally relates to methods for treating rhinosinusitis, including fungus-induced rhinosinusitis, viral-induced, bacterial-induced rhinosinusitis and/or non-bacterial, non-viral or non-fungus induced rhinosinusitis. In one alternative embodiment, an individual suffering from rhinosinusitis may be administered a steroidal agent of the present invention alone, or in combination or conjunction with an anti-fungal agent, antibiotic or antiviral agent. For example, the steroidal agent may be administered separately from the anti-fungal agent or antibiotic, or each of these ingredients may be administered simultaneously (e.g., in a single formulation) or individually, concurrently, in tandem or subsequently relative to each other, or in any combination thereof.

DETAILED DISCUSSION OF THE INVENTION

The present invention is directed to formulations for the treatment of one or more symptoms associated with rhinosinusitis in an individual. Rhinosinusitis may occur in the nasal mucosa and/or paranasal sinuses, or nasal-paranasal region, for example. Symptoms of rhinosinusitis may include, without limitation: inflammation, facial pain, pressure, fullness, nasal obstruction or blockage, nasal or postnasal discharge, rhinorrhea, fever, headaches, halitosis, fatigue, dental pain, cough, ear pain, pressure and/or fullness.

Nasal polyps may also be associated with or indicative of rhinosinusitis. Nasal polyps are outgrowths from the nasal-paranasal mucosa that are typically smooth, gelatinous, semi-translucent, round or pear shaped, and pale. In general, nasal polyps are located on the lateral wall of the nose, usually in the middle meatus or along the middle and superior turbinates. Most nasal polyps arise from the ethmoid sinus but some polyps originate in the maxillary sphenoid sinuses. The mass of a nasal polyp is composed mainly of edematous fluid with sparse fibrous cells and a few mucous glands. The surface epithelium of nasal and paranasal polyps generally reveals squamous metaplasia. Eosinophils are usually present in polyps in moderate to large numbers, and it is now known that nasal polyp fluid contains greater than normal concentrations of IgA, IgE, IgG, and IgM antibodies as well as abnormally high concentrations of IL-5, a cytokine that contributes to eosinophil activation and survival.

It is understood that the scope of the invention is directed to the treatment of rhinosinusitis including, but not limited to, any rhinosinusitis condition, including, but not limited to, acute, subacute, recurrent acute and chronic rhinosinusitis, which may be accompanied by, aggravated by, associated with or caused by (in whole or in part) fungi, viruses, or microorganisms in the mucosa. For example, rhinosinusitis may include fungus-induced rhinosinusitis caused by, for example, an immunologic response to mucosal fungi or other organism. In one alternative embodiment, the fungus-induced rhinosinusitis is allergic fungal rhinosinusitis, or AFS. In yet another example, rhinosinusitis may include non-fungal induced, non-bacterial induced, or non-viral induced rhinosinusitis.

In one alternative embodiment, the present invention is directed to formulations for the treatment of rhinosinusitis. In one embodiment, the formulations comprise an anti-inflammatory agent, alone or in combination with an antifungal agent, antibiotic or antiviral agent, or any combination thereof. As used herein, treatment means the prophylaxis, prevention or amelioration of one or more symptoms of, or associated with, rhinosinusitis, or any manner in which one or more of the symptoms of, or associated with, rhinosinusitis are beneficially altered or are prevented from worsening. As used herein, amelioration means any lessening, whether permanent or temporary, lasting or transient, of one or more symptoms of rhinosinusitis, including but not limited to fungus-induced rhinosinusitis, bacteria-induced rhinosinusitis, viral-induced rhinosinusitis, and rhinosinusitis that is not induced by an infective agent, such as fungus, bacteria, or virus.

Antifungal Agent

Antifungal agents for use herein include any agent effective in treating rhinosinusitis, including fungus-induced rhinosinusitis. Preferably, the antifungal agent of the present formulations reduces the presence of fungal organisms within mucus to a level such that the characteristic inflammatory responses and resulting damages associated with fungal induced rhinosinusitis are lessened, whether permanent or temporary, lasting or transient, stopped, treated, or prevented.

For example, in one alternative embodiment of the present invention, an antifungal agent for use herein may include any agent that prevents the growth of or kills a fungal organism such as antifungal polyene macrolides, tetraene macrolides, pentaenic macrolides, fluorinated pyrimidines, imidazoles, triazoles, azoles, halogenated phenolic ethers, thiocarbamates, and allylamines, and other. In addition, antifungal agents can be agents that interpolate fungal cell wall components or act as sterol inhibitors. Specific antifungal agents within the scope of the invention include, without limitation, amphotericin .beta., flucytosine, ketoconazole, miconazole, itraconazole, fluconazole, griseofulvin, clotrimazole, econazole, terconazole, butoconazole, oxiconazole, sulconazole, saperconazole, voriconazole, ciclopirox olamine, haloprogin, tolnaftate, naftifine, nystatin, natamycin, terbinafine hydrochloride, morpholines, butenafine undecylenic acid, Whitefield's ointment, propionic acid, and caprylic acid as well as those agents that can be identified as antifungal agents using methods well known in the art. Preferably, the antifungal agent of the present formulations is amphotericin .beta or fluconazole.

It is noted that a particular patient may possess a fungal organism acting as the etiological agent that is resistant to a particular antifungal agent. In such a case, an embodiment of this invention involves treating that patient with an effective antifungal agent (e.g., an antifungal agent that prevents the growth of, or kills, the fungal organism acting as the etiological agent). Such fungal organisms acting as etiological agents can be identified using collection and culture methods known in the art.

In one alternative embodiment, the formulation of the present invention may comprise any amount of antifungal agent that reduces, prevents, eliminates one or more symptoms of, or associated with, fungus-induced rhinosinusitis without producing significant toxicity. In one embodiment, an effective amount may be any amount greater than or equal to the minimum inhibitory concentration (MIC) for a fungal organism or isolate present within a particular individual's mucus that does not induce significant toxicity to the individual upon administration. Some antifungal agents may have a relatively large concentration range that is effective while others may have a relatively narrow effective concentration range. In addition, the effective amount can vary depending upon the specific fungal organism or isolate since certain organisms and isolates are more or less susceptible to particular antifungal agents. Such effective amounts can be determined for individual antifungal agents using commonly available or easily ascertainable information involving antifungal effectiveness concentrations, animal toxicity concentrations, and tissue permeability rates.

In one alternative embodiment, the formulation of the present invention may comprise any amount of an anti-inflammatory agent, such as fluticasone, that reduces, prevents, or eliminates inflammation, in combination with an antifungal agent. For example, non-toxic antifungal agents typically can be directly or indirectly administered in any amount that exhibits antifungal activity within mucus. In addition, antifungal agents that do not permeate mucosal epithelium typically may be directly administered to the mucus in any amount that exhibits antifungal activity within mucus. Using the information provided herein, such effective amounts also may be determined by routine experimentation in vitro or in vivo. For example, a patient having a fungus-induced rhinosinusitis can receive direct administration of an antifungal agent in an amount close to the MIC calculated from in vitro analysis. If the patient fails to respond, then the amount may be increased by, for example, ten fold. After receiving this higher concentration, the patient can be monitored for both responsiveness to the treatment and toxicity symptoms, and adjustments made accordingly.

In one embodiment, the present formulations comprise about 0.01 mg to about 1000 mg per kg of body weight of the mammal per administration of formulation, where the formulation is administered directly or indirectly to the nasal mucosa, paranasal sinuses, or nasal-paranasal mucosa. Antifungal agents particularly suitable for administration are itraconazole, ketoconazole, or voriconazole. The MIC values for voriconazole range from about 0.003 .mu.g/mL to about 4 .mu.g/mL depending upon the specific fungal organism or isolate tested. For fluconazole, the MIC values range from about 0.25 .mu.g/mL to greater than about 64 .mu.g/mL.

Various factors can influence the actual amount of antifungal agent in the formulations provided herein. For example, the frequency of administration of the formulations, duration of treatment, combination of other antifungal agents, site of administration, degree of inflammation, and the anatomical configuration of the treated area may require an increase or decrease in the actual amount of antifungal agent in the present formulations.

Table 1 sets forth non-limiting ranges and dosages of the antifungal agent that may be used in the present invention.

TABLE 1

Antifungal Agents and Dosages

| Generic Name | Class | Ranges |
|---|---|---|
| Amphotericin β | Antifungal | 0.5-150 mg; 4-30 mg; 7.5-15 mg; or 10 mg |
| Fluconazole | Antifungal | 0.5-150 mg; 12.5-150 mg; 20-70 mg; 25-50 mg; 10 mg; or 30 mg |
| Itraconazole | Antifungal | 0.5-150 mg; 20-70 mg; 25-50 mg; or 30 mg |

Anti-Inflammatory Agent

In one alternative embodiment, the formulation of the present invention may comprise a therapeutically effective amount of anti-inflammatory agent, or any pharmaceutically acceptable derivative thereof. In one embodiment of the present invention, a therapeutically effective amount of an anti-inflammatory agent for treating one or more symptoms of rhinosinusitis may include from about 10 mcg to about 2000 mcg. In an alternative embodiment, a therapeutically effective amount of an anti-inflammatory agent may include from about 10 mcg to about 50 mcg; about 50 mcg to about 100 mcg; about 100 mcg to about 150 mcg; about 150 mcg to about 200 mcg; about 200 mcg to about 250 mcg; about 250 mcg to about 300 mcg; about 300 mcg to about 350 mcg; about 350 mcg to about 400 mcg; about 400 mcg to about 450 mcg; about 450 mcg to about 500 mcg; about 500 mcg to about 550 mcg; about 550 mcg to about 600 mcg; about 600 mcg to about 650 mcg; about 650 mcg to about 700 mcg; about 700 mcg to about 750 mcg; about 750 mcg to about 800 mcg; about 800 mcg to about 850 mcg; about 850 mcg to about 900 mcg; about 900 mcg to about 950 mcg; about 950 mcg to about 1000 mcg; about 1000 mcg to about 1050 mcg; about 1050 mcg to about 1100 mcg; about 1100 mcg to about 1150 mcg; about 1150 mcg to about 1200 mcg; about 1200 mcg to about 1250 mcg; about 1250 mcg to about 1300 mcg; about 1300 mcg to about 1350 mcg; about 1350 mcg to about 1400 mcg; about 1400 mcg to about 1450 mcg; about 1450 mcg to about 1500 mcg; about 1500 mcg to about 1550 mcg; about 1550 mcg to about 1600 mcg; about 1600 mcg to about 1650 mcg; about 1650 mcg to about 1700 mcg; about 1700 mcg to about 1750 mcg; about 1750 mcg to about 1800 mcg; about 1800 mcg to about 1850 mcg; about 1850 mcg to about 1900 mcg; about 1900 mcg to about 1950 mcg; or about 1950 mcg to about 2000 mcg.

Anti-inflammatories for use herein include fluticasone, beclomethasone, any pharmaceutically acceptable derivative thereof, and any combination thereof. As used herein, a pharmaceutically acceptable derivative includes any salt, ester, enol ether, enol ester, acid, base, solvate, racemate or hydrate thereof. Such derivatives may be prepared by those of skill in the art using known methods for such derivatization.

In one alterative embodiment, the anti-inflammatory agents may have a specific particle size distribution profile. As used herein, particle size refers to an average particle size as measured by conventional particle size measuring techniques well known to those skilled in the art, such as, for example, microscopic assessment, cascade impaction technique, and the Malvern particle sizer.

In one alternative embodiment, the formulations of the present invention may also comprise an anti-inflammatory agent having the following particle size distribution profile:
  (i) about 10% of the drug substance may have a particle size less than about 0.05, 0.10, 0.15, 0.20, 0.25, 0.30, 0.35, 0.40, 0.50, 0.55, 0.60, 0.70, 0.75, 0.80, 0.90, 1.0, or 1.5, microns;
  (ii) about 25% of the drug substance may have a particle size less than about 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.60, 1.70, 1.80, 1.90, 2.0, 2.1, 2.2, 2.3, 2.4, or 2.5 microns;
  (iii) about 50% of the drug substance may have a particle size less than about 0.10, 0.20, 0.30, 0.40, 0.50, 0.60, 0.70, 0.80, 0.90, 1.0, 1.1, 1.2, 1.3, 1.4, 1.5, 1.6 1.7, 1.8, 1.9, 2.0, 2.1, 2.2, 2.3, 2.4, 2.5, 3.0, 3.2, 3.3, 3.4, 3.5, 3.6, 3.7, 3.8, 3.9, or 4.0 microns;
  (iv) about 75% of the drug substance may have a particle size less than about 0.10, 0.20, 0.30, 0.40, 0.50, 0.60, 0.70, 0.80, 0.90, 1.0, 1.2, 1.3, 1.4, 1.5, 1.6 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 4.0, 4.5, 5.0, 5.5, 6.0, 6.5, 7.0, 7.5, 8.0, or 8.5 microns;
  (v) about 90% of the drug substance particles have a size less than about 0.10, 0.20, 0.30, 0.40, 0.50, 0.60, 0.70, 0.80, 0.90, 1.0, 1.1, 1.2, 1.3, 1.4, 1.5, 1.6 1.7, 1.8, 1.9, 2.0, 2.1, 2.2, 2.3, 2.4, 2.5, 3.0, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7, 8, 9, and 10 microns; and or
  (vi) greater than about 90% to about 100% of the drug substance particles have a particle size more than 0.5, 1, 2, 3, 4, 5, 6, 7, 8, 9, 10, 11, 12, 13, 14, 15, 16, 17, 18, 19, or 20 microns.

Fluticasone

Preferably, the intranasal steroid of the present formulations is fluticasone propionate. Fluticasone propionate is a synthetic corticosteroid and has the empirical formula $C_{25}H_{31}F_3O_5S$. It has the chemical name S-(fluromethyl)6α, 9-difluoro-11β-17-dihydroxy-16α-methyl-3-oxoandrosta-1, 4-diene-17β-carbothioate, 17-propionate. Fluticasone propionate is a white to off-white powder with a molecular weight of 500.6 and is practically insoluble in water, freely soluble in dimethyl sulfoxide and dimethylformamide, and slightly soluble in methanol and 95% ethanol.

In an embodiment, the formulations of the present invention may comprise a steroidal anti-inflammatory (e.g., fluticasone propionate) having the following particle size distribution profile: preferably about 10% or less of the steroid particles have a particle size of less than 0.40 microns; about 25% or less of the steroid particles have a particle size of less than 1.4 microns; about 50% or less of the steroid particles have a particle size of less than 2.5 microns; about 75% or less of the steroid particles have a particle size of less than 4.0 microns; about 90% or less of the steroid particles have a particle size of less than 6.0 microns.

Beclomethasone

Also preferably, the steroidal anti-inflammatory of the present formulations is beclomethasone dipropionate or its monohydrate. Beclomethasone dipropionate has the chemical name 9-chloro-11 b, 17,21-trih-ydroxy-16b-methylpregna-1,4-diene-3,20-doine 17,21-dipropionate. The compound may be a white powder with a molecular weight of 521.25; and is very slightly soluble in water (Physicians' Desk Reference.RTM), very soluble in chloroform, and freely soluble in acetone and in alcohol.

The formulation of the present invention may comprise a steroidal anti-inflammatory (e.g., bellomethasome disproportionate) having the following particle size distribution profile; about 10% of the steroid particles have a particles size of less than about 0.40 microns; about 25% of the steroid particles have a particle size of less than 1.4 microns; about 50% of the steroid particles have a particle size of less than 2.5 microns; about 75% or less of the steroid particles have a particle size of less than 4.0 microns.

In another embodiment of the present invention about 90% or less of the steroid particles have a particle size of less than 6.0 microns; and greater than 90% or about 100% of the steroid particles have a particle size of less than 10 microns.

It is understood that each of the particle size distribution profiles described in application Ser. Nos. 10/657,550, 10/414,682 and 10/414,756, now U.S. Pat. No. 7,811,606 may be suitable for any of the anti-inflammatory agents described herein. The preferred anti-inflammatory agents are fluticasone and beclomethasone. In addition, the treatment regimens, mode of administrations, methods of treatment, dosages an other ingredients described in these applications may also be suitable for use in the formulations of the present invention. Each of these applications is incorporated herein by reference in their entirety.

Additionally, the formulations of the present invention may comprise an anti-inflammatory (e.g., fluticasone or beclomethasone) alone or in combination with one or more other steroidal anti-inflammatories. Examples of steroidal anti-inflammatories for use herein include, but are not limited to, Betamethasone, Triamcinolone, Dexamethasone, Prednisone, Mometasone, Flunisolide, Budesonide Ciclesomide, Lobedrednan and Etipredral. Non-limiting examples of anti-inflammatory agents and dosages that may be used for use herein are also listed in Table 2.

TABLE 2

Anti-inflammatory Agents and Dosages

| Generic Name | Class | Ranges |
| --- | --- | --- |
| Beclamethasone | Steroidal Anti-inflammatory | 0.1-4 mg; 0.2-3 mg; 0.2-2 mg; or 0.8 mg |
| Betamethasone | Steroidal Anti-inflammatory | 0.1-4 mg; 0.2-3 mg; 0.2-2 mg; or 0.8 mg |
| Dexamethasone | Steroidal Anti-inflammatory | 0.1-4 mg; 0.2-3 mg; 0.2-2 mg; or 0.8 mg |
| Flunisolide | Steroidal Anti-inflammatory | 0.1-4 mg; 0.2-3 mg; 0.2-2 mg; or 0.8 mg |
| Flurbiprofen | Nonsteroidal Anti-inflammatory | 0.01-2 mg; 0.05-1 mg; 0.1-0.5 mg; or 0.15 mg |
| Fluticasone | Steroidal Anti-inflammatory | 10-700 mcg; 25-400 mcg; 75-300 mcg; or 200 mcg |
| Ibuprofen | Nonsteroidal Anti-inflammatory | 25-400 mg; 30-300 mg; 50-150 mg; or 100 mg |
| Ketorolac | Nonsteroidal Anti-inflammatory | 0.05-4 mg; 0.1-2 mg; 0.3-1 mg; or 0.5 mg |

TABLE 2-continued

Anti-inflammatory Agents and Dosages

| Generic Name | Class | Ranges |
|---|---|---|
| Triamcinalone | Steroidal Anti-inflammatory | 0.05-3 mg; 0.2-2.5 mg; 0.5-2 mg; or 0.6 mg |

Anti-Infective Agents

The formulations of the present invention may further comprise an antibiotic or other anit-infective agent. Additionally, since more than one bacterial organism may be associated with the bacterial infection of the nasal mucosa, paranasal sinuses, or nasal-paranasal region, the present formulations may comprise a broad-spectrum antibiotic such as amoxicillin, erythromycin, or cefadroxil. Alternatively, a combination of anti-bacterial agents with differing spectra of activity may also be used. Non-limiting examples of antibiotics and dosages that may be used in the present invention are shown in Table 3 below.

TABLE 3

Anti-Infective Agents

| Generic Name | Class | Ranges |
|---|---|---|
| Amikacin | Amino glycoside | 50-500 mg; 1-800 mg; 75-300 mg; 5-500 mg; 100-200 mg; 50-300 mg; 166 mg'; or 150 mg |
| Amoxicillin | Broad spectrum | 19-2000 mg; 50-100 mg; 10-50 mg; or 50 BID |
| Amphotericin B | Antifungal | 2.5-45 mg; 4-30 mg; 7.5-15 mg; or 10 mg |
| Azithromycin | Macrolide | 50-400 mg; 25-400 mg; 75-300 mg; 150-200 mg; or 167 mg |
| Cefazolin | Cephlasporin (Gen I) | 250-1000 mg; 150-1000 mg; 300-900 mg; 575-700 mg; or 650 mg |
| Cefepine | Cephlasporin (Gen IV) | 125-1000 mg; 75-1000 mg; 200-900 mg; 575-700 mg; or 650 mg |
| Cefonicid | Cephlasporin (Gen II) | 250-1000 mg; 150-1000 mg; 300-900 mg; 575-700 mg; or 600 mg |
| Cefaperazone | Cephlasporin (Gen III) | 250-1000 mg; 150-1000 mg; 300-900 mg; 575-700 mg; or 600 mg |
| Cefotaxime | Cephlasporin (Gen III) | 250-1000 mg; 150-1000 mg; 300-900 mg; 575-700 mg; or 600 mg |

TABLE 3-continued

Anti-Infective Agents

| Generic Name | Class | Ranges |
|---|---|---|
| Cefotetan | Cephlasporin (Cephamycin) | 250-1000 mg; 150-1000 mg; 300-900 mg; 575-700 mg; or 600 mg |
| Cefoxitin | Cephlasporin (Cephamycin) | 250-1000 mg; 150-1000 mg; 300-900 mg; 575-700 mg; or 600 mg |
| Ceftazidime | Cephlasporin (Gen III) | 250-1000 mg; 150-1000 mg; 300-900 mg; 475-750 mg; or 550 mg |
| Ceftizoxime | Cephlasporin (Gen III) | 250-1000 mg; 150-1000 mg; 300-900 mg; 575-700 mg; or 600 mg |
| Ceftriaxone | Cephlasporin (Gen III) | 250-1000 mg; 150-1000 mg; 300-900 mg; 575-700 mg; or 650 mg |
| Cefuroxime | Cephlasporin (Gen II) | 100-600 mg; 50-600 mg; 200-520 mg; 250-400 mg; or 285 mg |
| Cephapirin | Cephlasporin (Gen I) | 250-1000 mg; 150-1000 mg; 300-900 mg; 575-700 mg; or 650 mg |
| Ciprofloxacin | Quinolone | 25-200 mg; 15-200 mg; 50-175 mg; 75-110 mg; or 90 mg |
| Clindamycin | Lincosamide | 50-600 mg; 25-600 mg; 75-500 mg; 125-300 mg; or 225 mg |
| Doxycycline | Tetracycline | 10-100 mg; 15-80 mg; 25-65 mg; or 27 mg |
| Erythromycin Lactobionate | Macrolide | 50-600 mg; 25-600 mg; 60-350 mg; 100-300 mg; or 150 mg |
| Fluconazole | Antifungal | 12.5-150 mg; 20-70 mg; 25-50 mg; or 30 mg |
| Gentamycin | Amino glycoside | 10-200 mg; 1-800 mg; 30-150 mg; 5-500 mg; 80-120 mg; 50-300 mg; 95 mg; or 150 mg |
| Itraconazole | Antifungal | 12.5-150 mg; 20-70 mg; 25-50 mg; 30 mg |
| Kanamycin | Amino glycoside | 1-800 mg; 5-500 mg; 50-300 mg; or 150 mg |

TABLE 3-continued

Anti-Infective Agents

| Generic Name | Class | Ranges |
|---|---|---|
| Levofloxacin | Quinolone | 40-200 mg; 50-150 mg; 60-80 mg; or 70 mg |
| Linezolid | Miscellaneous anti-bacterial | 50-600 mg; 25-600 mg; 75-450 mg; 100-300 mg; or 200 mg |
| Mezlocillin | Penicillin | 300-1500 mg; 100-1500 mg; 375-1000 mg; 750-950 mg; or 833 mg |
| Miconazole | Antifungal | 12.5-300 mg; 30-200 mg; 50-100 mg; or 60 mg |
| Mupirocin | Antibacterial | 1-25 mg; 1.5-20 mg; 2-15 mg; or 10 mg |
| Nafcillin | Penicillin | 250-1000 mg; 150-1000 mg; 300-900 mg; 575-700 mg; or 600 mg |
| Netilmicin | Amino glycoside | 1-800 mg; 5-500 mg; 50-300 mg; or 150 mg |
| Neomycin | Amino glycoside | 1-800 mg; 5-500 mg; 50-300 mg; or 150 mg |
| Ofloxacin | Quinolone | 25-200 mg; 50-175 mg; 75-110 mg; or 90 mg |
| Oxacillin | Penicillin | 250-1000 mg; 150-1000 mg; 300-900 mg; 575-700 mg; or 600 mg |
| Paromomycin | Amino glycoside | 1-800 mg; 5-500 mg; 50-300 mg; or 150 mg |
| Piperacillin | Penicillin | 100-1000 mg; 50-1000 mg; 125-750 mg; 250-600 mg; or 460 mg |
| Streptomycin | Amino glycoside | 1-800 mg; 5-500 mg; 50-300 mg; or 150 mg |
| Taurolin | Non-antibiotic antimicrobial | 5-200 mg; 20-150 mg; 40-120 mg; or 80 mg |
| Ticarcillin + Clavulanate | Penicillin | 500-5000 mg; 200-5000 mg; 1000-4000 mg; 1500-3500 mg; or 2250 mg |
| Tobramycin | Amino glycoside | 10-200 mg; 1-800 mg; 30-150 mg; 5-500 mg; 80-120 mg; 50-300 mg; 95 mg; or 150 mg |
| Vancomycin | Antibiotic-miscellaneous | 50-400 mg; 25-400 mg; 75-325 mg; 125-250 mg; or 166 mg |

Antiviral Agents

The formulations of the present invention may comprise a therapeutically effective amount of one or more antiviral agents. These agents can be administered individually or simultaneously with the steroidal agent of the present invention. The antiviral agent may also include Acyclovir, Famciclovir, Valacyclovir, edoxudine, ganciclovir, foscarnet, cidovir (vistide), Vitrasert, Formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N-,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazolyl]-methane), and NIH351.

Other suitable dosages and methods of treatment of the ingredients described herein are described in U.S. 2001/0006944A1, publication date Jul. 4, 2001, which is incorporated herein by reference in its entirety.

Other Components

The formulations of the present invention may also comprise mucolytic, anticolinergics, antihistamine, monobactans, mast stabilizer, carbapenen, antilleukotriene, decongestant and antiseptic agents. Non-limiting examples of such components and dosages that may be used in the present invention are listed in Table 4.

TABLE 4

| Generic Name | Class | Ranges |
|---|---|---|
| Acetylcysteine | Mucolytics | 125-500 mg; 150-450 mg; 200-400 mg; or 300 mg |
| Atropine | Anticolinergic | 10-700 mcg; 25-400 mcg; 75-30 mcg; or 200 mcg |
| Azelastine | Antihistamine | 137-1096 mcg; 204-822 mcg; 382-616 mcg; or 411 mcg |
| Aztreonan | Monobactam | 250-1000 mg; 300-900 mg; 475-750 mg; or 450 mg |
| Cromolyn Sodium | Mast cell stabilizer | 5-100 mg; 7.5-75 mg; 10-50 mg; or 20 mg |

TABLE 4-continued

| Generic Name | Class | Ranges |
| --- | --- | --- |
| Dornase alpha | Mucolytic | 0.5-5 mg; 1-4 mg; 2-3 mg; or 1.5 mg |
| Ipratropium | Anticholinergic | 10-700 mcg; 25-400 mcg; 75-300 mcg; or 200 mcg |
| Meropenem | Carbapenem | 200-75 mg; 250-700 mg; 300-500 mg; or 33 mg |
| Montelukast | Antileukotriene | 0.5-15 mg; 2-25 mg; 3-15 mg; or 10 mg |
| Nedocromil | Mast cell stabilizer | 1-25 mg; 3-15 mg; 5-12 mg; or 7 mg |
| Oxymetazoline | Decongestant | 0.05-0.5 mg; 0.075-0.4 mg; 0.1-0.3 mg; or 0.2 mg |
| Phenylepherine | Decongestant | 5-50 mg; 10-35 mg; 15-20 mg; or 10 mg |
| Potassium Iodide | Antiseptic | 30-200 mg; 40-150 mg; 50-80 mg; or 60 mg |
| Rifampin | Miscellaneous | 500-5000 mg; 1000-4000 mg; 1500-3500 mg; or 2250 mg |
| Tetrahydrozolidine | Decongestant | 0.05-0.5 mg; 0.06-0.4 mg; 0.1-0.3 mg; or 0.15 mg |
| Xylometazoline | Decongestant | 0.05-0.4 mg; 0.075-03 mg; 0.1-0.2 mg; or 0125 mg |
| Zafirlukast | Antileukotriene | 2-60 mg; 4-50 mg; 6-30 mg; or 20 mg |

The formulation of the present invention may be in any form provided the formulation can be administered to a mammal in an amount, at a frequency, and for a duration effective to prevent, reduce, or eliminate one or more symptoms associated with rhinosinusitis. For example, a formulation within the scope of the invention may be in the form of a solid, liquid, and/or aerosol including, without limitation, powders, crystalline substances, gels pastes, ointments, salves, creams, solutions, suspensions, partial liquids, sprays, nebulae, mists, atomized vapors, tinctures, pills, capsules, tablets, and gel-caps. In addition, the formulation can contain a cocktail of other ingredients, particularly those described herein. For example, a formulation within the scope of the invention can contain, without limitation, one, two, three, four, five, or more different anti-inflammatory agents, antifungal agents, antibiotics, antiviral agents, or the other ingredients described herein, or any combination thereof. Further, formulations within the scope of the invention may contain additional ingredients including, without limitation, pharmaceutically acceptable aqueous vehicles, pharmaceutically acceptable solid vehicles, steroids, mucolytic agents, antibacterial agents, anti-inflammatory agents, immunosuppressants, dilators, vaso-constrictors, decongestants, leukotriene inhibitors, anti-cholinergics, anti-histamines, therapeutic compounds and combinations thereof. Such antiviral agents may include IMPDH inhibitors, inhibitors of virus adsorption entry, inhibitors of fusion with host cells, antisense oligonucleotides, and nucleoside analogues.

In one embodiment, the present formulations may be provided in any form suitable for intranasal administration. In another alternative embodiment, the formulations of the present invention are in solution or suspension form suitable for intranasal administration.

In an embodiment, the formulation of the present invention may comprise a preservative, suspending agent, wetting agent, tonicity agent and/or diluent. In one embodiment, the formulations provided herein may comprise from about 0.01% to about 95%, or about 0.01% to about 50%, or about 0.01% to about 25%, or about 0.01% to about 10%, or about 0.01% to about 5% of one or more pharmacologically suitable suspending fluids which is physiologically acceptable upon administration. Pharmacologically suitable fluids for use herein may include, but are not limited to, polar solvents, including, but not limited to, compounds that contain hydroxyl groups or other polar groups. Solvents may include, but are not limited to, water or alcohols, such as ethanol, isopropanol, and glycols including propylene glycol, polyethylene glycol, polypropylene glycol, glycol ether, glycerol and polyoxyethylene alcohols. Polar solvents may also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in drugs.

In certain embodiments herein, the formulations of the present invention have a pH of about 2.0 to about 9.0, preferably about 3.0 to about 7.0. Optionally, the formulations of the present invention may contain a pH buffer. For example, a buffer may comprise any known pharmacologically suitable buffers that are physiologically acceptable upon administration intranasally. The buffer may be added to maintain the pH of the formulation between about 3.0 and about 7.0, for example.

Sterility or adequate antimicrobial preservation may be provided as part of the present formulations. Since certain formulations of the present invention are intended to be administered intranasally, it is preferred that they be free of pathogenic organisms. A benefit of a sterile liquid suspension is that it reduces the possibility of introducing contaminants into the individual when the suspension formulation is administered intranasally, thereby reducing the chance of an opportunistic infection. Processes that may be considered for achieving sterility may include any appropriate sterilization steps known in the art.

In one embodiment, the formulation of the present invention may be produced under sterile conditions, and the micronization of the steroidal anti-inflammatory may be performed in a sterile environment, and the mixing and packaging may be conducted under sterile conditions. In one alternative embodiment, one or more ingredients in the present formulation may be sterilized by steam, gamma radiation or prepared using or mixing sterile steroidal powder and other sterile ingredients where appropriate. In addition, the formulations may be prepared and handled under sterile conditions, or may be sterilized before or after packaging.

In addition to or in lieu of sterilization, the formulations of the present invention may contain a pharmaceutically acceptable preservative to minimize the possibility of microbial contamination. Additionally, a pharmaceutically acceptable preservative may be used in the present formulations to increase the stability of the formulations. It should be noted, however, that any preservative must be chosen for safety, as the treated tissues may be sensitive to irritants. Preservatives suitable for use herein may include, but are not limited to, those that protect the solution from contamination with pathogenic particles, including phenylethyl alcohol, benzalkonium chloride, benzoic acid, or benzoates such as sodium benzoate. In certain embodiments, the formulations herein may comprise from about 0.01% and about 1.0% w/w of benzalkonium chloride, or from about 0.01% and about 1% v/w phenylethyl alcohol. Preserving agents may also be present in an amount from about 0.01% to about 1%, preferably about 0.002% to about 0.02% by total weight or volume of the formulation.

The formulations provided herein may also comprise from about 0.01% to about 90%, or about 0.01% to about 50%, or about 0.01% to about 25%, or about 0.01% to about 10%, or about 0.01% to about 1% w/w of one or more emulsifying agent, wetting agent or suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerized soya bean oil; and pectin extract. In certain embodiments herein, the present formulations comprise polysorbate 80, microcrystalline cellulose, carboxymethylcellulose sodium and/or dextrose.

The present formulations may further comprise from about 0.01% to about 90%, or about 0.01% to about 50%, or about 0.01% to about 25%, or about 0.01% to about 10%, or about 0.01% to about 1% w/w of one or more excipients and additives that are pharmacologically suitable. Excipients and additives generally have no pharmacological activity, or at least no undesirable pharmacological activity. The concentration of these may vary with the selected agent, although the presence or absence of these agents, or their concentration is not an essential feature of the invention. The excipients and additives may include, but are not limited to, surfactants, moisturizers, stabilizers, complexing agents, antioxidants, tonicity agents or other additives known in the art.

Complexing agents include, but are not limited to, ethylenediaminetetraacetic acid (EDTA) or a salt thereof, such as the disodium salt, citric acid, nitrilotriacetic acid and the salts thereof. In another embodiment, particularly in the suspension formulations provided herein, the complexing agent is sodium edetate. In one embodiment, the compositions contain sodium edetate at a concentration of about 0.05 mg/mL to about 0.5 mg/mL, or about 0.1 mg/mL to about 0.2 mg/mL. In addition, for example, the formulations of the present invention may comprise from about 0.001% to about 5% by weight of a humectant to inhibit drying of the mucous membrane and to prevent irritation. Any of a variety of pharmaceutically acceptable humectants can be employed, including sorbitol, propylene glycol, polyethylene glycol, glycerol or mixtures thereof, for example.

The formulations provided herein also may comprise about 0.01% to about 90%, or about 0.01% to about 50%, or about 0.01% to about 25%, or about 0.01% to about 10%, or about 0.01% to about 10% w/w of one or more solvents or co-solvents to increase the solubility of any of the components of the present formulations. Solvents or co-solvents for use herein include, but are not limited to, hydroxylated solvents or other pharmaceutically acceptable polar solvents, such as alcohols including isopropyl alcohol, glycols such as propylene glycol, polyethylene glycol, polypropylene glycol, glycol ether, glycerol, and polyoxyethylene alcohols. In another embodiment, the formulations of the present invention may comprise one or more conventional diluents known in the art. The preferred diluent is purified water.

Tonicity agents may include, but are not limited to, sodium chloride, potassium chloride, zinc chloride, calcium chloride and mixtures thereof. Other osmotic adjusting agents may also include, but are not limited to, mannitol, glycerol, and dextrose or mixtures thereof. In an alternative embodiment, the present formulation may comprise about 0.01% to about 10% w/w, or about 1% to about 8% w/w, or 1% to about 6% w/w, preferably about 5.0% w/w. The preferred tonicity agent is anhydrous dextrose.

In one alternative embodiment, the formulations of the present invention are stable. As used herein, the stability of formulations provided herein refers to the length of time at a given temperature that greater than 80%, 85%, 90% or 95% of the initial amount of the active ingredient(s) is present in the formulation. For example, the formulations provided herein may be stored between about 15° C. and about 30° C., and remain stable for at least 1, 2, 12, 18, 24 or 36 months. Also, the formulations may be suitable for administration to a subject in need thereof after storage for more than 1, 2, 12, 18, 24 or 36 months at 25° C. Also, in another alternative embodiment, using Arrhenius Kinetics, more than 80%, or more than 85%, or more than 90%, or more than 95% of the initial amount of active ingredients remains after storage of the formulations for more than 1, 2, 12, 18, 24 or 36 months between about 15° C. and about 30° C.

The formulations of the present invention may be manufactured in any conventional manner known in the art, or by minor modification of such means. For example, the formulations may be manufactured by thoroughly mixing the ingredients described herein at ambient or elevated temperatures in order to achieve solubility of ingredients where appropriate.

The preparation of the steroidal inflammatory of the present invention, e.g., fluticasone propionate and beclomethasone dipropionate, having a specific particle size distribution profile may be obtained by any conventional means known in the art, or by minor modification of such means. For example, suspensions of drug particles can rapidly undergo particulate size reduction when subjected to "jet milling"

(high-pressure particle in liquid milling) techniques. Other known methods for reducing particle size into the micrometer range include mechanical milling, the application of ultrasonic energy and other techniques.

In addition, the formulations of the present invention may comprise any of the following components: (i) antihistamine: (ii) non-steroidal anti-flammatories; (iii) decongestants; (iv) mucolytics; (v) anticholinergics; or (vi) mass cell stabilizers. Examples of such components are found in U.S. 2002/0061281 A1, published May 23, 2002. This reference is incorporated herein by reference in its entirety.

In one alternative embodiment, the present invention is directed to a pharmaceutical composition that may be useful in treating rhinosinusitis caused by Alpha Hemolytic Sreptococci, Beta Hemolytic Streptococci, Branhamella Catarrhalis, Diptheroids, Heaemophilis influenza (beta-lactamase positive and negative), *Moraxella* species, *Psuedomonas aeroguinosa, Pseudomas maltophilia, Serratia marcesns, Staphylococcus aureus, Streptococcus pheumonia, Aspergillosis, Mucor* and *Candida albicans, Flusarium, Curvularia, crytococcus, coccidiodes*, and *histoplasma*.

Mode of Administration

The present formulations may be packaged for administration in any conventional manner, preferably in a nasal applicator, and preferably in such a way as to deliver a fixed dose of drug substance (e.g., active ingredient). However, the present formulations may be administered via a nasal application in such a way as to deliver a non-fixed dose of drug substance. In one embodiment, the present formulations may be delivered through the intranasal route (as described herein) so as to contact directly or indirectly the nasal mucosa and/or paranasal sinuses.

Spray Administration containers for various types of nasal formulations have been known in the past and substantially all will be equally suitable for the present formulations, considering of course that the materials from which the container is made is compatible with the formulations. The medium containing the drug substance and other appropriate ingredients may be contained in a small bottle or similar container, from which it can be dispersed as a mist to be directed into each nostril. Using ambient air as the propelling agent, one may have the bottle made of a flexible plastic, so that merely squeezing the bottle's sides impels the spray out through the nozzle into the nasal cavity. Air may also be the propelling agent for a pump sprayer, in which the user manipulates a small pump button that pumps air into the container and causes the liquid spray to be emitted on the return stroke. Alternatively, the bottle can be pressurized with a gas that is inert to the user and to the ingredients of the solution. The gas may be dissolved under pressure in the container or may be generated by dissolution or reaction of a solid material that forms the gas as a product of dissolution or as a reaction product. Typical gases that may be used include nitrogen, argon, and carbon dioxide. Also, when the formulation is administered as a spray or aerosol, the formulation may be contained in a pressurized container with a liquid propellant including, but not limited to dicholorodifluoro methane or chlorotrifluoro ethylene, among other propellants.

In another alternative embodiment, for administration as a spray, the present formulations may be placed in an appropriate atomizing device, e.g. in a pump-atomizer or the like. The atomizing device may be provided with appropriate means for delivery of aqueous spray to the naris. Preferably, it is provided with means ensuring delivery of a substantially fixed volume of composition/actuation (i.e. per spray-unit). In one embodiment, the device administers a metered dosage. The spray composition may be suspended or dissolved in a liquid propellant. Stabilizing and/or suspending agents and/or co-solvents may be present. In other embodiments herein, the formulation of the present invention is suitable for administration intranasally via a metered-dose spray pump to a subject in need thereof. In this respect, the formulation of the present invention may be pre-packaged in a metered-dose spray pump bottle, or metering atomizing pump.

In another alternative embodiment, the formulations of the present invention may be administered into the nose in the form of drops, or any other method that results in topical application to the nasal mucosa. The form of dosage for intranasal administration may include solutions, suspensions or emulsions of the active compound in a liquid carrier in the form of nose drops. Suitable liquid carriers include water, propylene glycol and other pharmaceutically acceptable alcohols. For administration in drop form formulations may suitably be put in a container provided e.g. with a conventional dropper/closure device, e.g. comprising a pipette or the like, preferably delivering a substantially fixed volume of composition/drop. The dosage forms may be sterilized, as required. The dosage forms may also contain adjuvants such as preservatives, stabilizers, emulsifiers or suspending agents, wetting agents, salts for varying the osmotic pressure or buffers, as required.

Other modes of administration may include, without limitation, nasal irrigations, nasal sprays, nasal inhalations, and nasal packs with, for example, saturated gauze. In addition, injections into the nasal-paranasal cavities using, for example, a needle or catheter tube may be employed. Any device can be used to directly administer the present formulations intranasally including, without limitation, a syringe, bulb, inhaler, canister, spray can, nebulizer, and mask.

Other modes of administration to the nasal-paranasal anatomies may also include, without limitation, oral, intravenous, intradermal, and intraperitoneal administrations provided the administered agent contacts nasal-paranasal mucosa. In addition, any device can be used to administer an agent to the nasal-paranasal anatomy including, without limitation, a syringe and regulated release capsule.

The present formulations may be packaged in any conventional manner suitable for administration of the present formulations. Spray administration containers for various types of nasal formulations have been known in the past and substantially all will be equally suitable for the present formulations, provided that the container materials is compatible with the formulation. In an embodiment, the formulation of the present invention herein is packaged in a container such that it can be dispersed as a mist to be directed into each nostril. For example, the container may be made of flexible plastic such that squeezing the bottle's sides impels the spray out through the nozzle into the nasal cavity. Alternatively, a small pump button may pump air into the container and cause the liquid spray to be emitted on the return stroke when pressed.

In an alternative embodiment, the formulations of the present invention are packaged in a container pressurized with a gas that is inert to the user and to the ingredients of the solution. The gas may be dissolved under pressure in the container or may be generated by dissolution or reaction of a solid material that forms the gas as a product of dissolution or as a reaction product. Suitable inert gases that may be used herein include nitrogen, argon, and carbon dioxide. Also, the formulations herein may be administered as a spray or aerosol wherein the formulation is packaged in a pressurized container with a liquid propellant such as dicholorodifluoro methane or chlorotrifluoro ethylene, or other propellant.

In another embodiment of the present invention, the present formulations are packaged in a metered dose spray pump, or metering atomizing pump, such that each actuation of the pump delivers a fixed volume of the formulation (i.e. per spray-unit). For administration in drop or other topical form, the formulations herein may suitably be packaged in a container provided with a conventional dropper/closure device, comprising a pipette or the like, preferably delivering a substantially fixed volume of the formulation.

In another alternative embodiment, the inhalation solution of the present invention may be administered by nebulizer. Such nebulizer including, but not limited to, a jet nebulizer, ultrasonic nebulizer and an actuated nebulizer. In one embodiment, the nebulizer being equipped with a suitable facemask for nasal administration. In yet another embodiment, the nebulizer may have a facemask associated with the chamber of the nebulizer, or a facemask positioned in close proximity to the individual's face. The formulation may be passed in a mist form from the nebulizer chamber through the facemask to the individual while the individual breathes into the facemask through his/her nose. The individual continues breathing into the facemask until the nebulization treatment is finished. This may take about or less than about 12, 11, 10, 9, 8, 7, 6, 5, 4, 3, 2, 1 or 0.5 minutes, or any range therebetween. In another alternative embodiment, the treatment may be finished in about 60, 50, 40, 30, 20, 10, 5 or 1 second, or any range therebetween. In an alternative embodiment, the nebulization treatment is finished when at least substantially all the mist is removed from the nebulizer chamber. This may take about or less than about 12, 11, 10, 9, 8, 7, 6, 5, 4, 3, 2, 1 or 0.5 minutes, or any range therebetween. In an alternative embodiment, it may take about 60, 50, 40, 30, 20, 10, 5 or 1 second, or any range therebetween.

Method of Treatment

The present invention is also directed to a method for treating rhinosinusitis, including fungus-induced rhinosinusitis, bacterial-induced rhinosinusitis, viral-induced rhinosinusitis, and rhinosinusitis that is not induced by an infective agent, such as bacteria, fungus or virus. In one embodiment, the method of treating rhinosinusitis of the present invention comprises the step of administering a therapeutically effective amount of the formulation of the present invention to a mammal in need thereof. The formulation may comprise an anti-inflammatory agent of the present invention alone or in combination with an anti-fungal agent, an antibiotic or antiviral agent. The formulation is preferably administered intranasally. In one embodiment, the formulation is administered directly or indirectly to the nasal mucosa, paranasal sinuses, or the nasal-paranasal mucosa. In an alternative embodiment, the formulation is administered intranasally via a metered dose spray pump. In general, the course of treatment for any individual with respect to any of the active ingredients described herein can be readily determined by his or her physician.

The method of the present invention may further comprise administering the present formulation for a duration or frequency sufficient to treat one or more symptoms of rhinosinusitis. For example, the formulation may be administered one time to about 10 times a day for about one day to about 100 days or more, or until the symptoms of interest have lessened, for example. In an embodiment, the method of the present invention comprises administering to a mammal diagnosed with rhinosinusitis (e.g., not induced by an infective agent) is a formulation comprising a therapeutically effective amount of an anti-inflammatory agent intranasally via a spray pump or any other drug delivery device one to three times a day for up to two weeks. In an alternative embodiment, the administration of the present formulations may comprise 1, 2, 3, 4, 5, 6, 7 or 8 intranasal applications of the present formulation one, two, three, four or five times a day.

Most pharmaceutical inhalation solutions may contain the anti-microbial agent BAC. One problem with these solutions is that the BAC may cause undesirable adverse effects if the solution is administered repeatedly over short intervals. The formulation of the present invention may be provided without BAC, thereby making it suitable, especially in an emergency situation, where the inhalation solution is administered repeatedly over a short period of time. Also, administering a BAC-free inhalation solution to a patient reduces the concomitant liability of adverse effects associated with BAC. It also reduces the toxicity and other side effects associated with BAC.

The formulation of the present invention may also be provided in sterile, unit dose treatments, thus eliminating the need to include BAC in the solution. Moreover, in sterile form the formulation of the present invention (which comprises, for example, a therapeutically effective amount of an anti-inflammatory agent) may provide a stable inhalation solution such that the formulation can be stored (e.g., on a shelf) for long periods of time.

In one alternative embodiment, the formulations provided herein are stable. For example, the compositions provided herein may be stored between about 15° C. and about 30° C., and remain stable for a relatively long period of time. In one embodiment, the formulations may be stored at 25° C.

In another embodiment, the stability of the formulations provided herein may contain greater than 80%, 85%, 90% or 95% of the initial amount of active ingredient, e.g., Fluticasone propionate, at a given temperature for a long period of time. Thus, for example, a composition that is stable for 30 days at 25° C. would have greater than 80%, 85%, 90% or 95% of the initial amount of active ingredients present in the composition at 30 days following storage at 25° C.

In another embodiment, the formulations herein may be stable during long term storage, in that the formulations are suitable for administration to a subject in need thereof when they have been stored for a length of time (i.e., shelf-life) for a period greater than 1, 2 or 3 years at 25° C. In other embodiments herein, using Arrhenius Kinetics, >80% or >85% or >90% or >95% estimated active ingredient remains after such storage, for example.

In another embodiment, the formulation of the present invention may have a pH of about 2.0 to about 8.0. In another embodiment of the claimed invention, the formulation may have a pH of about 3.0 to about 4.0, preferably a pH of about 3.5. The pH may be adjusted with 1N hydrochloric acid or 1N sulfuric acid. The formulation solution of the present invention may also contain sodium citrate (e.g. sodium citrate dihydrate at a concentration of about 0.1 to 0.5% (w/w), preferably about 0.2% (w/w). Other excipients may include acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES, BIS-TRIS, ADA, ACES, PIPES, MOPSO, BIS-TRIS PROPANE, BES, MOPS, TES, HEPES, DIPSO, MOBS, TAPSO, TRIZMA, HEPPSO, POPSO, TEA, EPPS, TRICINE, GLY-GLY, BICINE, HEPBS, TAPS, and AMPD buffers.

In another embodiment of the present invention, the osmolality of the inhalation solution may be adjusted from about 150 to about 550 mOsm/kg. In other embodiments of the present invention, the osmolality of the solution may be from about 275 to about 325 mOsm/kg. In yet another embodiment, the composition may have an osmolality of about 290 mOsm/kg. Tonicity adjusting agents include but are not limited to the following excipients: ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethyl sulfoxide, edetate disodium, edetate trisodium monohydrate, fluorescein sodium, fructose, galactose, glycerin, lactic acid, lactose, magnesium chloride, magnesium sulfate, manitol, polyethyne glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine, and zinc sulfate.

In one embodiment, the formulation of the present invention is sterile. A benefit of a sterile inhalation solution is that it reduces the possibility of introducing contaminants into the patient when administered, thereby reducing the chance of an opportunistic infection in the patient.

Non-adherence to medication therapy and medication error is considerable problems. These problems can be significantly reduced by providing patients a prepackaged, premixed, premeasured amount of an anti-inflammatory agent or other active ingredients albuterol and ipratropium. Providing these compounds in this fashion makes rhinosinusitis therapy simple because it increases convenience and eliminates confusion in preparing appropriate dosages. These advantages are especially significant where treatments often come in multiple dosage units and must be diluted to specific concentrations suitable for treating patients.

The present invention may overcome the aforementioned problems by providing therapeutically effective amounts of an anti-inflammatory agent or other active ingredients (such as those described herein) in prepackaged, premixed, premeasured and/or unit dose amounts. In one embodiment, the present invention comprises one or more prefilled containers. The one or more containers may comprise a single unit dose of an aqueous solution comprising a therapeutically effective amount of anti-inflammatory agents or other active ingredient(s) for the treatment of rhinosinusitis. Providing the formulation in such a manner eliminates the need to dilute or mix medications to obtain proper dosages for treatment. Also, no special pharmacy compounding is required, thereby reducing the chance of medication errors. Further, there is a lower risk of cross-contamination, and less waste of medication when providing the formulation of the present invention in a premixed, ready to use form.

The present invention may be designed to facilitate user compliance by providing one or more dispensing containers comprising a premixed, premeasured formulation comprising a single unit dose of a therapeutically effective amount of one or more active ingredients for the treatment of rhinosinusitis. Such containers may be utilized in a method of treating rhinosinusitis or the containers may be incorporated in a system and/or kit for treating the same.

In one alternative embodiment, the present invention is a sterile, premixed, premeasured, BAC-free formulation comprising a single unit dose of a therapeutically effective amount of an anti-inflammating agent, anti-viral agent, anti-fungal agent and/or anti-bacterial agent, alone or in any combination thereof in a single container. Sodium chloride may be added to make the solution isotonic and hydrochloric acid may be added to adjust pH of the solution to an appropriate range. The formulation of the present invention may or may not include a chelating agent, such as EDTA.

In another alternative embodiment, the formulation of the present invention may be supplied as a 0.1 ml to a 3 ml, sterile, BAC-free, solution (e.g., nebulizable solution). The nebulizer solution may be contained in a unit-dose, low-density polyethylene (LDPE) container. Each unit-dose container may be disposed in a foil pouch, and each foil pouch may contain 5 or more unit-dose containers. Each foil pouch containing the unit dose container may be disposed in a shelf carton.

In another alternative embodiment, the present invention comprises a prepackaged system and/or kit suitable for patients suffering from rhinosinusitis. Such prepackaged system and/or kit comprising: (a) one or more single unit dosages of a therapeutically effective amount of one or more active ingredients; (b) administration instructions for the use of said unit dose as a treatment for symptoms associated with rhinosinusitis; and (c) a dispensing container prefilled with a unit dose of one or more active ingredients suitable for treating one or more symptoms associated with rhinosinusitis.

In another alternative embodiment, the prepackaged inhalation system and/or kit of the present invention provides one or more premixed, premeasured single unit dose vials comprising a therapeutically effective amount of one or more suitable active ingredients for the treatment of symptoms associated with rhinosinusitis, and optionally comprising instructions for using the same.

The present invention is also directed to a method of treating symptoms associated with rhinosinusitis, wherein a therapeutically effective amount of one or more active ingredients may be administered as a unit dose. Such unit dose may be in the form of a nebulizer solution or a solution suitable for administration by a spray pump, or any other device capable of intranasal administration.

Osmotic adjusting agents that may be used include, but are not limited to, sodium chloride, potassium chloride, zinc chloride, calcium chloride and mixtures thereof. Other osmotic adjusting agents may also include, but are not limited to, mannitol, glycerol, and dextrose and mixtures thereof. In an alternative embodiment, the present invention may comprise about 0.4 to about 1.0 weight percent ionic salt.

The present formulation may be contained into one or more dispensing vials, each vial being filled with about 0.1 ml to about 5 ml, or about 0.1 ml to about 2.25 ml, or about 0.1 ml to about 3.0 ml, about 0.5 ml to about 3.0 ml, or about 0.5 ml to about 2.0 ml, or about 0.1 ml to about 2 ml, preferably about 0.5 ml to about 1 ml, about 2 ml, or about 3 ml of the formulation of the present invention such that the solution in the each vial comprises one or more unit doses of a therapeutically effective amount of active ingredient(s) suitable for treating rhinosinusitis. Also, in another alternative embodiment, the stability of the solution in the one or more dispensing containers is such that the solution is therapeutically effective following storage for 12 months at 25° C. The solution may be suitable for intranasal administration via nebulizer, spray pump, metered dose spray pump, or any other means by which the present formulation can be administered intranasally.

In one alternative embodiment, the volume of the of the present invention is about 0.1 ml to about 2.25 ml, or about 0.1 ml to about 2 ml, or about 1 ml to about 2 ml, about 1.5 ml to about 2 ml, preferably about 1 ml, about 1.5 ml, about 2.0 ml, or about 2.25 ml, about 2.5 ml, about 3.0 ml, about 3.5 ml, about 4.0 ml, about 4.5 ml, or about 5.0 ml. In another alternative embodiment, the volume of the of the present invention may be about 0.05 ml to about 1.0 ml; 0.1 ml to about 0.9 ml; 0.1 ml to about 0.8 ml; 0.1 ml to about 0.7 ml; 0.1 ml to about 0.6 ml; 0.1 ml to about 0.5 ml; 0.1 ml to about 0.4 ml; 0.1 ml to about 0.3 ml; 0.1 ml to about 2.0 ml. In one embodiment the fill volume of the formulation of the present invention is from about 0.05 ml to about 0.4 ml, from about 0.1 ml to about 3.0 ml.

In another alternative embodiment, the system of the present invention comprises one or more dispensing containers prefilled with about 0.1 ml to about 2.0 ml, or about 0.1 ml to about 1.0 ml; 0.1 ml to about 0.9 ml; 0.1 ml to about 0.8 ml; 0.1 ml to about 0.7 ml; 0.1 ml to about 0.6 ml; 0.1 ml to about 0.5 ml; 0.1 ml to about 0.4 ml; 0.1 ml to about 0.3 ml; 0.1 ml to about 2.0 ml; about 0.5 ml to about 2.0 ml, or about 0.1 ml to about 2.25 ml, or about 1.0 ml to about 2.0 ml, or about 2.0 ml to about 2.4 ml or about 2.5 ml to about 3.0 ml of a premixed, premeasured, aqueous inhalation solution comprising a single unit dose of a therapeutically effective amount of one or more active ingredients, including but not limited to, anti-bacterial, anti-fungal, anti-viral or anti-inflammatory agent for treating one or more symptoms associated with rhinosinusitis.

In one alternative embodiment, the formulation of the present invention may be provided with a label, which may comprise indicia comprising efficacy, dosage, administration, contraindication and adverse reaction data pertaining to the formulation in each of the one or more containers. The contraindication data may comprise data indicating that the formulation in each of the one or more containers is contraindicated for humans with hypersensitivity to any of the ingredients contained in the formulation. The dosage and administration data may also comprise data indicating that the recommended dose of the formulation in each of the one or more containers may be administered 1, 2, 3, 4, 5, 6, 7 or 8 times per day by nebulization, spray pump or any other suitable means for administering the formulation intranasally.

In one alternative embodiment, the present invention is also directed to a method of reducing medication error and enhancing therapeutic compliance of an individual suffering from rhinosinusitis. In one such embodiment, the method comprises the step of administrating to the individual at least one or more dispensing vials of the formulation described herein, for example. Dispensing vials may include, but are not limited to, any container comprising glass, low density polyethylene, or any other material capable of preventing the solution from leaking out of the container. The vial may be enclosed by any conventional means, including but not limited to, screw cap, heat seal, snap-on top, flip-top, twist-off stopper, peel away top, and the like.

In another alternative embodiment, the present formulation may be stored in or dispensed from any dispensing vial made of suitable plastic material. For example, the dispensing vial may be constructed of any suitable elastomeric material, such as olefin-based materials, including but not limited to, polyethylene, ethylene-propylene copolymers, ethylene-vinyl acetate copolymers, ethylene-acrylic ester copolymers, ionomers, and combinations thereof. Furthermore, polymers having barrier properties, such as polyvinylidene chloride and ethylene-vinyl alcohol copolymers, as well as polymers such as polyvinyl chloride, polyester, polyamide and polyurethanes may also be used.

EXAMPLES

Examples 1-6 herein are prophetic examples provided to illustrate, but not limit, the formulations and methods of the present invention. They are presented with the understanding that changes can be and may need to be made to a specific composition in order to obtain or optimize the formulation. Such modifications to the following prophetic examples, if needed, are normal and understandable to those of ordinary skill in the art, and shall not be used to limit the invention.

It is believed that prophetic examples 1-6 would be suitable for intranasal administration to an individual suffering from rhinosinusitis that is not associated with a bacterial, viral or fungal infection, or to an individual suffering from rhinosinusitis associated with a fungal, viral or bacterial infection. The formulations may be sterile. It is understood that the steroid, antibiotic, antifungal agent or the other ingredients described herein may be administered in the same formulation, or may be administered individually, or in any combination thereof.

Example 1

| | |
|---|---|
| Fluticason | about 10-2000 mcg/ml |
| Polysorbyte 80 | about 0-1 mg/ml |
| Disodium EDTA, USP | about 1 mg/ml |
| Nacitrate Dihydrate, USP | about 0.065 mg/ml |
| NACI, USP | about 8.8 mg/ml |
| Purified Water, USP | q.s |

Example 1 is a prophetic example of a formulation of the present invention that may be used for treating symptoms associated with rhinosinusitis such as, for example, rhinosinusitis not induced by an infective agent, such as bacteria, fungus or virus, wherein about 10% of the fluticasone propionate particles have a particle size of less than 0.40 microns; about 25% of the fluticasone propionate particles have a particle size of less than 1.40 microns; about 50% of the fluticasone propionate particles have a particle size of less than 2.5 microns; about 75% of the fluticasone propionate particles have a particle size of less than 4.0 microns; and about 90% of the fluticasone propionate particles have a particle size of less than 6.0 microns. The formulation of Example 1 may be made by methods known to those or ordinary skill in the art.

Example 2

| | |
|---|---|
| Amphotericin B | about 2.0-about 100.0 mg/ml |
| Neomycin Sulfate | about 5.0-about 100.0 mg/ml |
| Fluticasone Propionate | about 0.25-about 1.0 mg/ml |
| Polysorbate 80 | about 0.1-about 1.0 mg/ml |
| Purified Water | q.s. |

Example 2 is a prophetic example of a formulation of the present invention that may be used for treating symptoms associated with rhinosinusitis, such as for example, fungus-induced or bacterial-induced rhinosinusitis. The formulation of Example 2 may be made by methods known to those of ordinary skill in the art.

Example 3

| | |
|---|---|
| Fluconazole | about 1.0-about 20.0 mg/ml |
| Neomycin Sulfate | about 5.0-about 100.0 mg/ml |
| Phenylethyl Alcohol | about 0.5-about 10.0 mg/ml |
| Fluticasone Propionate | about 0.25-about 1.0 mg/ml |
| Microcrystalline Cellulose | about 5.0-about 15.0 mg/ml |
| Polysorbate 80 | about 0.1-about 1.0 mg/ml |
| Purified Water | q.s. |

Example 3 is a prophetic example of a formulation of the present invention for treating symptoms associated with rhinosinusitis, such as, for example, fungus-induced or bacteria-induced rhinosinusitis, wherein about 10% of the fluticasone propionate particles have a particle size of less than 0.40 microns; about 25% of the fluticasone propionate particles have a particle size of less than 1.40 microns; about 50% of the fluticasone propionate particles have a particle size of less than 2.5 microns; about 75% of the fluticasone propionate particles have a particle size of less than 4.0 microns; and about 90% of the fluticasone propionate particles have a particle size of less than 6.0 microns. The solution of Example 3 may be made by methods known to those of ordinary skill in the art.

Example 4

| | |
|---|---|
| Amphotericin B | about 2.0-about 100.0 mg/ml |
| Neomycin Sulfate | about 5.0-about 100.0 mg/ml |
| Benzalkonium Chloride | about 0.1-about 0.5 mg/ml |
| Dextrose | about 20.0-about 100.0 |
| Phenylethyl Alcohol | about 0.5-about 10.0 mg · ml |
| Beclomethasone Dipropionate | about 0.25-about 1.0 mg/ml |
| Purified Water | q.s. |

Example 4 is a prophetic example of a formulation of the present invention for treating symptoms associated with rhinosinusitis, such as, for example, fungus-induced or bacteria-induced rhinosinusitis, wherein about 10% of the beclomethasone dipropionate particles have a particle size less than 0.40 microns; about 25% of the beclomethasone dipropionate particles have a particle size less than 1.40 microns; about 50% of the beclomethasone dipropionate particles have a particle size less than 2.5 microns; about 75% of the beclomethasone dipropionate particles have a particle size less than 4.0 microns; about 90% of the beclomethasone dipropionate particles have a particle size less than 6.0 microns; and greater than 90% or about 100% of the beclomethasone dipropionate particles have a particle size less than 6.0 microns. Example 4 may be made by methods known to those of ordinary skill in the art.

Example 5

| | |
|---|---|
| Fluconazole | about 1.0-about 20.0 mg/ml |
| Neomycin Sulfate | about 5.0-about 100.0 mg/ml |
| Benzalkonium Chloride | about 0.1-about 0.5 mg/ml |
| Dextrose | about 20.0-about 100.0 |
| Beclomethasone Dipropionate | about 0.25-about 1.0 mg/ml |
| Purified Water | q.s. |

Example 5 is a prophetic example of a formulation of the present invention for treating symptoms associated with rhinosinusitis, such as, for example, fungus-induced or bacteria-induced rhinosinusitis, wherein about 10% of the beclomethasone dipropionate particles have a particle size less than 0.40 microns; about 25% of the beclomethasone dipropionate particles have a particle size less than 1.40 microns; about 50% of the beclomethasone dipropionate particles have a particle size less than 2.5 microns; about 75% of the beclomethasone dipropionate particles have a particle size less than 4.0 microns; and about 90% of the beclomethasone dipropionate particles have a particle size less than 6.0 microns; and greater than 90% or about 100% of the beclomethasone dipropionate particles have a particle size less than 6.0 microns. Example 5 may be made by methods known to those of ordinary skill in the art.

Example 6

| | |
|---|---|
| Fluconazole | about 1.0-about 20.0 mg/ml |
| Benzalkonium Chloride | about 0.1-about 0.5 mg/ml |
| Dextrose | about 20.0-about 100.0 |
| Phenylethyl Alcohol | about 0.5-about 10.0 mg · ml |
| Beclomethasone Dipropionate | about 0.25-about 1.0 mg/ml |
| Purified Water | q.s. |

Example 6 is a prophetic example of a formulation of the present invention for treating symptoms associated with rhinosinusitis, such as, for example, fungus-induced or bacteria-induced rhinosinusitis, wherein about 10% of the beclomethasone dipropionate particles have a particle size less than 0.40 microns; about 25% of the beclomethasone dipropionate particles have a particle size less than 1.40 microns; about 50% of the beclomethasone dipropionate particles have a particle size less than 2.5 microns; about 75% of the beclomethasone dipropionate particles have a particle size less than 4.0 microns; and about 90% of the beclomethasone dipropionate particles have a particle size less than 6.0 microns; and greater than 90% or about 100% of the beclomethasone dipropionate particles have a particle size less than 6.0 microns. Example 6 may be made by methods known to those of ordinary skill in the art.

The Examples herein are presented for illustrative purposes only. They are not intended to limit the scope of the invention. Further, it should be understood that various changes and modifications to the embodiment described herein will be apparent to those skilled in the art. Such changes and modifications can be made without departing from the spirit and scope of the present invention and without diminishing its attendant advantages. It is therefore intended that such changes and modifications be covered by the appended claims. Also, the invention may suitably comprise, consist of or consist essentially of the elements or steps described herein. Further, the invention described herein suitably may comprise or be practiced in the absence of any element or step which is or is not specifically disclosed herein. Further, one or more step described herein may be performed simultaneously with another step, or may be performed individually.

What is claimed is:

1. A formulation for the treatment of symptoms associated with rhinosinusitis in a mammal suffering from rhinosinusitis, the formulation comprising an aqueous suspension comprising:
   (a) about 10 mcg to about 2000 mcg of an anti-inflammatory agent, the anti-inflammatory agent comprises suspended solid particles of fluticasone or pharmaceutically acceptable salt thereof, said suspended solid particles of fluticasone comprise the following particle size distribution profile:
   i. about 10% of the anti-inflammatory particles has an average particle size of less than 0.40 microns;
   ii. about 25% of the anti-inflammatory particles have an average particle size of less than 0.8 microns;
   iii. about 50% of the anti-inflammatory particles have an average particle size of less than 1.5 microns;
   iv. about 75% of the anti-inflammatory particles have an average particle size of less than 3.0 microns; and v. about 90% of the anti-inflammatory particles have an average particle size distribution of less than 5.3 microns; and (b) an antifungal agent, wherein the formulation is suitable for administration by the intranasal route of the mammal; wherein the formulation is sterile and free of benzalkonium chloride.

2. A formulation for the treatment of symptoms associated with rhinosinusitis in a mammal suffering from said rhinosinusitis, the formulation comprising an aqueous suspension comprising:

(a) about 10 mcg to about 2000 mcg of an anti-inflammatory agent, the anti-inflammatory agent comprises suspended solid particles of beclomethasone or pharmaceutically acceptable salt thereof, said suspended solid particles of beclomethasone comprise the following particle size distribution profile:
  i. about 10% of the anti-inflammatory particles has an average particle size of less than 0.30 microns;
  ii. about 25% of the anti-inflammatory particles have an average particle size of less than 0.55 microns;
  iii. about 50% of the anti-inflammatory particles have an average particle size of less than 1.1 microns; and
  iv. about 75% of the anti-inflammatory particles have an average particle size of less than 1.8 microns; and
  v. about 90% of the anti-inflammatory particles have an average particle size distribution of less than 2.7 microns; and (b) an antifungal agent, wherein the formulation is suitable for administration by the intranasal route of the mammal; wherein the formulation is sterile and free of benzalkonium chloride.

3. The formulation of claims 1 or 2, comprising about 25 mcg to about 400 mcg of the anti-inflammatory agent.

4. The formulation of claims 1 or 2, comprising about 75 to about 300 mcg of the anti-inflammatory agent.

5. The formulation of claims 1 or 2, comprising about 200 mcg of the anti-inflammatory agent, and wherein the formulation is sterile and free of benzalkonium chloride yet has a relatively long period of stability such that after storage for 12 months at a temperature between 15 to 30° C., greater than 80% of the anti-inflammatory agent and greater than 80% of the antifungal agent originally present in the formulation still remains in the formulation.

6. A formulation for the treatment of symptoms associated with rhinosinusitis in a mammal suffering thereof, the formulation comprises an aqueous suspension that comprises an anti-inflammatory agent, the anti-inflammatory agent comprises 0.04% to 0.06% by weight of suspended solid particles of fluticasone or pharmaceutically acceptable salt thereof, said suspended solid particles of fluticasone comprise the following particle size distribution profile:
  i. about 10% of the anti-inflammatory particles have an average particle size of less than 0.40 microns;
  ii. about 25% of the anti-inflammatory particles have an average particle size of less than 0.8 microns;
  iii. about 50% of anti-inflammatory particles have an average particle size of less than 1.5 microns;
  iv. about 75% of the anti-inflammatory particles have a particle size of less than 3.0 microns;
  v. about 90% of the anti-inflammatory particles have a particle size of less than 5.3 microns;

an antifungal agent, wherein the formulation is suitable for the administration by the intranasal route of the mammal; wherein the formulation is sterile and free of benzalkonium chloride.

7. A formulation for the treatment of symptoms associated with rhinosinusitis in a mammal suffering thereof, the formulation comprises an aqueous suspension that comprises an anti-inflammatory agent, the anti-inflammatory agent comprises 0.04% to 0.05% by weight of suspended solid particles of beclomethasone or pharmaceutically acceptable salt thereof, said suspended solid particles of beclomethasone comprise the following particle size distribution profile:
  i. about 10% of the anti-inflammatory particles have an average particle size of less than 0.30 microns;
  ii. about 25% of anti-inflammatory particles have an average particle size of less than 0.55 microns;
  iii. about 50% of the anti-inflammatory particles have an average particle size of less than 1.1 microns;
  iv. about 75% of the anti-inflammatory particles have a particle size of less than 1.8 microns;
  v. about 90% of the anti-inflammatory particles have a particle size of less than 2.7 microns;

an antifungal agent, wherein the formulation is suitable for the administration by the intranasal route of the mammal; wherein the formulation is sterile and free of benzalkonium chloride.

8. The formulations of claims 6 or 7, comprising about 25 mcg to about 400 mcg of the anti-inflammatory agent.

9. The formulation of claims 6 or 7, comprising about 75 mcg to about 300 mcg of the anti-inflammatory agent.

10. The formulations of claims 6 or 7, comprising about 200 mcg of said anti-inflammatory agent.

11. The formulations of claims 9 or 10, wherein the formulation is sterile and free of benzalkonium chloride yet has a relatively long period of stability such that after storage for 12 months at a temperature between 15 to 30° C., greater than 95% of the anti-inflammatory agent and greater than 95% of the antifungal agent originally present in the formulation still remains in the formulation.

12. The formulations of claims 9 or 10, wherein the formulation is suitable for intranasal administration by a spray pump, by nebulization or metered dose spray pump.

13. The formulation of claims 1, 2, 9 or 10, further comprising about 0.01% to about 90% by weight on a dried weight basis of one or more of the following compounds:
  (a) polysorbate 80;
  (b) disodium edetate dihydrate, USP;
  (c) sodium citrate dihydrate, USP;
  (d) sodium chloride, USP; and
  (e) purified water, USP.

14. The formulation of claim 13, wherein the:
  (a) polysorbate 80 is present in an amount of about 0.4 mg/ml;
  (b) disodium edetate dihydrate, USP is present in an amount of about 1 mg/ml;
  (c) sodium citrate dihydrate, USP is present in an amount of about 0.065 mg/ml; and
  (d) sodium chloride, USP is present in an amount of about 8.8 mg/ml.

15. The formulation of claim 13, wherein said formulation is a sterile aqueous suspension suitable for administration to the nasal-paranasal mucosa.

16. The formulations of claims 9 or 10, further comprising an antiviral agent.

* * * * *

UNITED STATES PATENT AND TRADEMARK OFFICE
CERTIFICATE OF CORRECTION

PATENT NO. : 8,309,061 B2
APPLICATION NO. : 11/078263
DATED : November 13, 2012
INVENTOR(S) : Chaundry It is certified that error appears in the above-identified patent and that said Letters Patent is hereby corrected as shown below:

In the Specifications:

Column 12,
Line 18, "foscamet" should read --foscarnet--.

In the Claims:

Column 27,
Line 59, "50% of anti-inflammatory particles" should read --50% of the anti-inflammatory particles--.

Column 28,
Line 14, "25% of anti-inflammatory particles" should read --25% of the anti-inflammatory particles--;
Lines 32, 39, and 62, "claims 9 or 10" should read --claims 6 or 7--;
Line 42, "claims 1, 2, 9 or 10" should read --claims 1, 2, 6, or 7--.

Signed and Sealed this
Fourteenth Day of May, 2013

Teresa Stanek Rea
*Acting Director of the United States Patent and Trademark Office*